United States Patent
Fessler

(10) Patent No.: US 11,207,193 B2
(45) Date of Patent: *Dec. 28, 2021

(54) OBLIQUE EXPANDING FUSION CAGE DEVICE AND METHOD

(71) Applicant: IN QUEUE INNOVATIONS, LLC, Winona Lake, IN (US)

(72) Inventor: Richard G. Fessler, Winnetka, IL (US)

(73) Assignee: IN QUEUE INNOVATIONS, LLC, Winona Lake, IN (US)

( * ) Notice: Subject to any disclaimer, the term of this patent is extended or adjusted under 35 U.S.C. 154(b) by 219 days.

This patent is subject to a terminal disclaimer.

(21) Appl. No.: 16/532,409

(22) Filed: Aug. 5, 2019

(65) Prior Publication Data

US 2019/0358050 A1 Nov. 28, 2019

Related U.S. Application Data

(63) Continuation of application No. 15/911,674, filed on Mar. 5, 2018, now Pat. No. 10,369,012, which is a
(Continued)

(51) Int. Cl.
*A61F 2/44* (2006.01)
*A61F 2/28* (2006.01)
*A61F 2/30* (2006.01)

(52) U.S. Cl.
CPC ...... *A61F 2/447* (2013.01); *A61F 2002/2835* (2013.01); *A61F 2002/30092* (2013.01);
(Continued)

(58) Field of Classification Search
CPC .......... A61F 2/44; A61F 2/442; A61F 2/4425; A61F 2/4455; A61F 2/446; A61F 2/4465;
(Continued)

(56) References Cited

U.S. PATENT DOCUMENTS 4,863,476 A * 9/1989 Shepperd .............. A61F 2/4455
623/17.15
5,059,193 A 10/1991 Kuslich
(Continued)

FOREIGN PATENT DOCUMENTS

| EP | 1415623 | 5/2004 |
| WO | 2013070427 | 5/2013 |
| WO | 2014078737 | 5/2014 |

OTHER PUBLICATIONS

International Search Report and Written Opinion of the International Searching Authority for PCT/US2013/070427, dated Feb. 26, 2014, 13 pages.
(Continued)

*Primary Examiner* — Eric S Gibson
(74) *Attorney, Agent, or Firm* — Heslin Rothenberg Farley & Mesiti P.C.; Jacquelyn A. Graff, Esq.

(57) ABSTRACT

An oblique expanding fusion cage device including a body with a superior portion and an inferior portion. The superior portion and the inferior portion have a proximal end and a distal end. The fusion cage device also includes a pathway, an opening, and an expanding member. The pathway travels from the proximal end to the distal end of the device between the superior and inferior portions. The opening in the proximal end of the body enables access to the pathway. The expanding member may be re movably inserted into the opening and is moveable toward the distal end of the body, wherein the expanding member engages the superior portion and the inferior portion as the expanding member moves distally within the pathway.

20 Claims, 26 Drawing Sheets

Related U.S. Application Data continuation of application No. 14/442,974, filed as application No. PCT/US2013/070427 on Nov. 15, 2013, now Pat. No. 9,907,671.

(60) Provisional application No. 61/727,504, filed on Nov. 16, 2012.

(52) U.S. Cl.
CPC .............. A61F 2002/30153 (2013.01); A61F 2002/30158 (2013.01); A61F 2002/30433 (2013.01); A61F 2002/30451 (2013.01); A61F 2002/30462 (2013.01); A61F 2002/30482 (2013.01); A61F 2002/30484 (2013.01); A61F 2002/30494 (2013.01); A61F 2002/30515 (2013.01); A61F 2002/30579 (2013.01); A61F 2002/30601 (2013.01); A61F 2002/30624 (2013.01); A61F 2002/30925 (2013.01); A61F 2310/00017 (2013.01); A61F 2310/00023 (2013.01)

(58) Field of Classification Search
CPC ............... A61F 2/447; A61F 2002/443; A61F 2002/4475
See application file for complete search history.

(56) References Cited

U.S. PATENT DOCUMENTS

| | | | |
|---|---|---|---|
| 5,554,191 A * | 9/1996 | Lahille | A61B 17/1757 |
| | | | 623/17.11 |
| 5,665,122 A | 9/1997 | Kambin | |
| 6,117,174 A | 9/2000 | Nolan | |
| 6,129,763 A | 10/2000 | Chauvin | |
| 6,368,351 B1 * | 4/2002 | Glenn | A61F 2/4455 |
| | | | 623/17.15 |
| 6,371,989 B1 | 4/2002 | Chauvin | |
| 6,395,031 B1 | 5/2002 | Foley | |
| 6,436,140 B1 * | 8/2002 | Liu | A61F 2/4611 |
| | | | 623/17.11 |
| 6,436,142 B1 | 8/2002 | Paes | |
| 6,443,989 B1 * | 9/2002 | Jackson | A61F 2/447 |
| | | | 623/17.15 |
| 6,454,807 B1 * | 9/2002 | Jackson | A61F 2/447 |
| | | | 623/17.15 |
| 6,491,724 B1 | 12/2002 | Ferree | |
| 6,562,074 B2 * | 5/2003 | Gerbec | A61F 2/4611 |
| | | | 623/17.15 |
| 6,648,917 B2 | 11/2003 | Gerbec | |
| 6,652,584 B2 * | 11/2003 | Michelson | A61F 2/4455 |
| | | | 623/17.11 |
| 6,656,178 B1 | 12/2003 | Veldhuizen | |
| 6,666,891 B2 * | 12/2003 | Boehm, Jr. | A61F 2/447 |
| | | | 623/17.16 |
| 6,685,742 B1 * | 2/2004 | Jackson | A61F 2/447 |
| | | | 623/17.11 |
| 6,709,458 B2 * | 3/2004 | Michelson | A61F 2/446 |
| | | | 623/17.15 |
| 6,723,128 B2 * | 4/2004 | Uk | A61F 2/446 |
| | | | 623/17.15 |
| 6,730,126 B2 | 5/2004 | Boehm, Jr. | |
| 6,743,255 B2 | 6/2004 | Ferree | |
| 6,773,460 B2 | 8/2004 | Jackson | |
| 6,821,298 B1 * | 11/2004 | Jackson | A61F 2/4611 |
| | | | 623/17.15 |
| 6,835,206 B2 | 12/2004 | Jackson | |
| 6,852,129 B2 | 2/2005 | Gerbec | |
| 6,863,673 B2 | 3/2005 | Gerbec | |
| 6,875,213 B2 | 4/2005 | Michelson | |
| 6,905,512 B2 | 6/2005 | Paes | |
| 6,955,691 B2 | 10/2005 | Chae | |
| 6,972,035 B2 * | 12/2005 | Michelson | A61F 2/446 |
| | | | 623/17.11 |
| 7,008,453 B1 | 3/2006 | Michelson | |
| 7,018,415 B1 * | 3/2006 | McKay | A61F 2/4455 |
| | | | 623/17.15 |
| 7,128,760 B2 | 10/2006 | Michelson | |
| 7,211,112 B2 | 5/2007 | Baynham | |
| 7,217,291 B2 * | 5/2007 | Zucherman | A61F 2/4425 |
| | | | 623/17.15 |
| 7,217,293 B2 | 5/2007 | Branch, Jr. | |
| 7,220,280 B2 | 5/2007 | Kast | |
| 7,410,501 B2 | 8/2008 | Michelson | |
| 7,431,735 B2 | 10/2008 | Liu | |
| 7,445,636 B2 | 11/2008 | Michelson | |
| 7,655,027 B2 | 2/2010 | Michelson | |
| 7,655,046 B2 * | 2/2010 | Dryer | A61F 2/4611 |
| | | | 623/17.15 |
| 7,678,148 B2 * | 3/2010 | Peterman | A61F 2/4455 |
| | | | 623/17.11 |
| 7,727,280 B2 * | 6/2010 | McLuen | A61F 2/4455 |
| | | | 623/17.16 |
| 7,828,848 B2 | 11/2010 | Chauvin | |
| 7,850,733 B2 | 12/2010 | Baynham | |
| 7,875,078 B2 | 1/2011 | Wysocki | |
| 7,879,098 B1 * | 2/2011 | Simmons, Jr. | A61F 2/4465 |
| | | | 623/17.11 |
| 7,993,403 B2 | 8/2011 | Foley | |
| 8,080,041 B2 * | 12/2011 | Boehm, Jr. | A61F 2/447 |
| | | | 606/279 |
| D664,252 S | 7/2012 | Weiland | |
| 8,221,502 B2 | 7/2012 | Branch, Jr. | |
| 8,267,939 B2 | 9/2012 | Cipoletti | |
| 8,273,129 B2 | 9/2012 | Baynham | |
| 8,303,658 B2 | 11/2012 | Peterman | |
| 8,333,804 B1 | 12/2012 | Wensel | |
| 8,349,014 B2 | 1/2013 | Barreiro | |
| 8,403,990 B2 | 3/2013 | Dryer | |
| 8,435,299 B2 | 5/2013 | Chauvin | |
| 8,460,385 B1 | 6/2013 | Wensel | |
| 8,523,944 B2 * | 9/2013 | Jimenez | A61F 2/447 |
| | | | 623/17.15 |
| 8,641,767 B2 | 2/2014 | Landry | |
| 8,647,386 B2 * | 2/2014 | Gordon | A61B 17/701 |
| | | | 623/17.15 |
| 8,685,095 B2 * | 4/2014 | Miller | A61F 2/447 |
| | | | 623/17.11 |
| 8,709,086 B2 * | 4/2014 | Glerum | A61F 2/4611 |
| | | | 623/17.16 |
| 8,936,641 B2 * | 1/2015 | Cain | A61F 2/447 |
| | | | 623/17.16 |
| 9,034,041 B2 * | 5/2015 | Wolters | A61B 17/8858 |
| | | | 623/17.15 |
| 9,259,328 B2 * | 2/2016 | Pabst | A61F 2/4455 |
| 9,414,934 B2 * | 8/2016 | Cain | A61F 2/442 |
| 9,907,671 B2 * | 3/2018 | Fessler | A61F 2/447 |
| 10,369,012 B2 * | 8/2019 | Fessler | A61F 2/447 |
| 2002/0010511 A1 * | 1/2002 | Michelson | A61F 2/4455 |
| | | | 623/17.15 |
| 2002/0068977 A1 * | 6/2002 | Jackson | A61F 2/4455 |
| | | | 623/17.15 |
| 2003/0208275 A1 * | 11/2003 | Michelson | A61F 2/4455 |
| | | | 623/17.16 |
| 2004/0030389 A1 * | 2/2004 | Ferree | A61F 2/30734 |
| | | | 623/17.15 |
| 2005/0021041 A1 * | 1/2005 | Michelson | A61F 2/4611 |
| | | | 606/90 |
| 2005/0113916 A1 * | 5/2005 | Branch, Jr. | A61F 2/447 |
| | | | 623/17.11 |
| 2005/0209698 A1 * | 9/2005 | Gordon | A61B 17/7023 |
| | | | 623/17.15 |
| 2005/0234555 A1 * | 10/2005 | Sutton | A61F 2/4455 |
| | | | 623/17.15 |
| 2005/0283248 A1 * | 12/2005 | Gordon | A61F 2/4425 |
| | | | 623/17.16 |
| 2006/0069442 A1 * | 3/2006 | Michelson | A61F 2/447 |
| | | | 623/17.15 |
| 2006/0253201 A1 * | 11/2006 | McLuen | A61F 2/447 |
| | | | 623/17.15 |

(56) References Cited

U.S. PATENT DOCUMENTS

| | | | |
|---|---|---|---|
| 2007/0106385 A1* | 5/2007 | Zucherman | A61B 17/7065 623/17.13 |
| 2008/0051902 A1* | 2/2008 | Dwyer | A61F 2/442 623/17.16 |
| 2008/0140207 A1* | 6/2008 | Olmos | A01H 5/12 623/17.16 |
| 2008/0294171 A1 | 11/2008 | Boehm, Jr. | |
| 2009/0088852 A1* | 4/2009 | Chee | A61F 2/442 623/17.16 |
| 2010/0049324 A1* | 2/2010 | Valdevit | A61F 2/447 623/17.16 |
| 2010/0185291 A1* | 7/2010 | Jimenez | A61F 2/4611 623/17.16 |
| 2010/0286780 A1 | 11/2010 | Dryer | |
| 2011/0035011 A1* | 2/2011 | Cain | A61F 2/4611 623/17.16 |
| 2011/0046682 A1* | 2/2011 | Stephan | A61B 17/8685 606/305 |
| 2011/0172277 A1 | 7/2011 | Bradford | |
| 2011/0172774 A1* | 7/2011 | Varela | A61F 2/4611 623/17.16 |
| 2011/0224796 A1 | 9/2011 | Weiland | |
| 2011/0301712 A1* | 12/2011 | Palmatier | A61F 2/4611 623/17.16 |
| 2012/0029637 A1* | 2/2012 | Ragab | A61F 2/447 623/17.11 |
| 2013/0310941 A1 | 11/2013 | Chauvin | |
| 2014/0156007 A1* | 6/2014 | Pabst | A61F 2/4611 623/17.16 |
| 2014/0277473 A1* | 9/2014 | Perrow | A61F 2/447 623/17.15 |
| 2014/0336764 A1* | 11/2014 | Masson | A61B 17/863 623/17.15 |
| 2015/0088258 A1* | 3/2015 | Jimenez | A61F 2/4455 623/17.15 |
| 2015/0094812 A1* | 4/2015 | Cain | A61F 2/447 623/17.15 |
| 2015/0100124 A1* | 4/2015 | Whipple | A61F 2/4455 623/17.15 |
| 2015/0182347 A1* | 7/2015 | Robinson | A61F 2/447 623/17.15 |
| 2015/0257894 A1* | 9/2015 | Levy | A61F 2/4611 623/17.15 |
| 2015/0328008 A1* | 11/2015 | Fessler | A61F 2/447 623/17.16 |
| 2016/0015522 A1* | 1/2016 | Arnin | A61F 2/4425 623/17.15 |
| 2018/0193161 A1* | 7/2018 | Fessler | A61F 2/447 |
| 2019/0358050 A1* | 11/2019 | Fessler | A61F 2/447 |

OTHER PUBLICATIONS

International Preliminary Report on Patentability for PCT/US2013/070427, dated May 19, 2015, 9 pages.

* cited by examiner

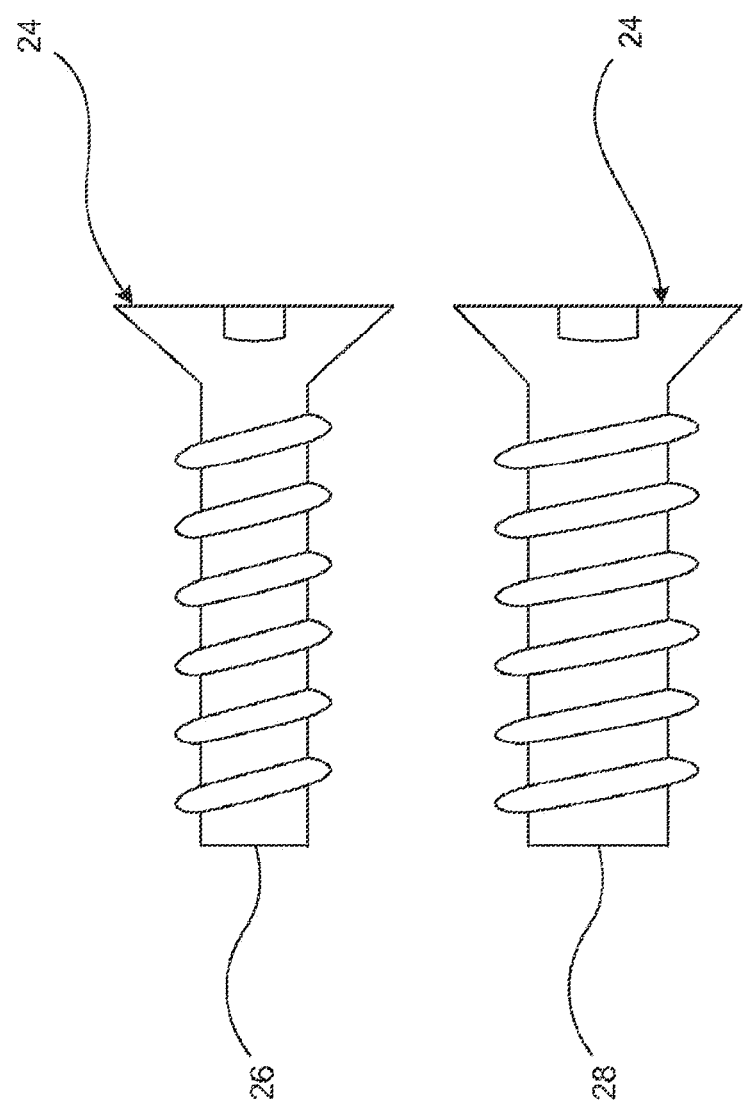

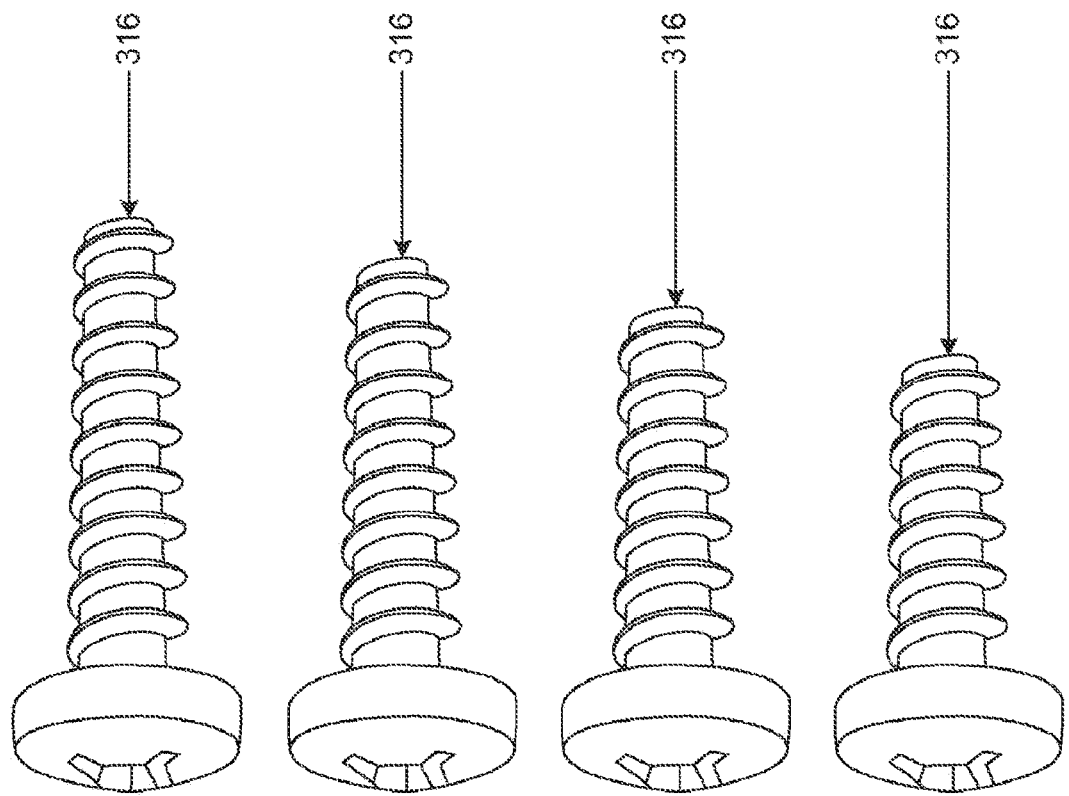

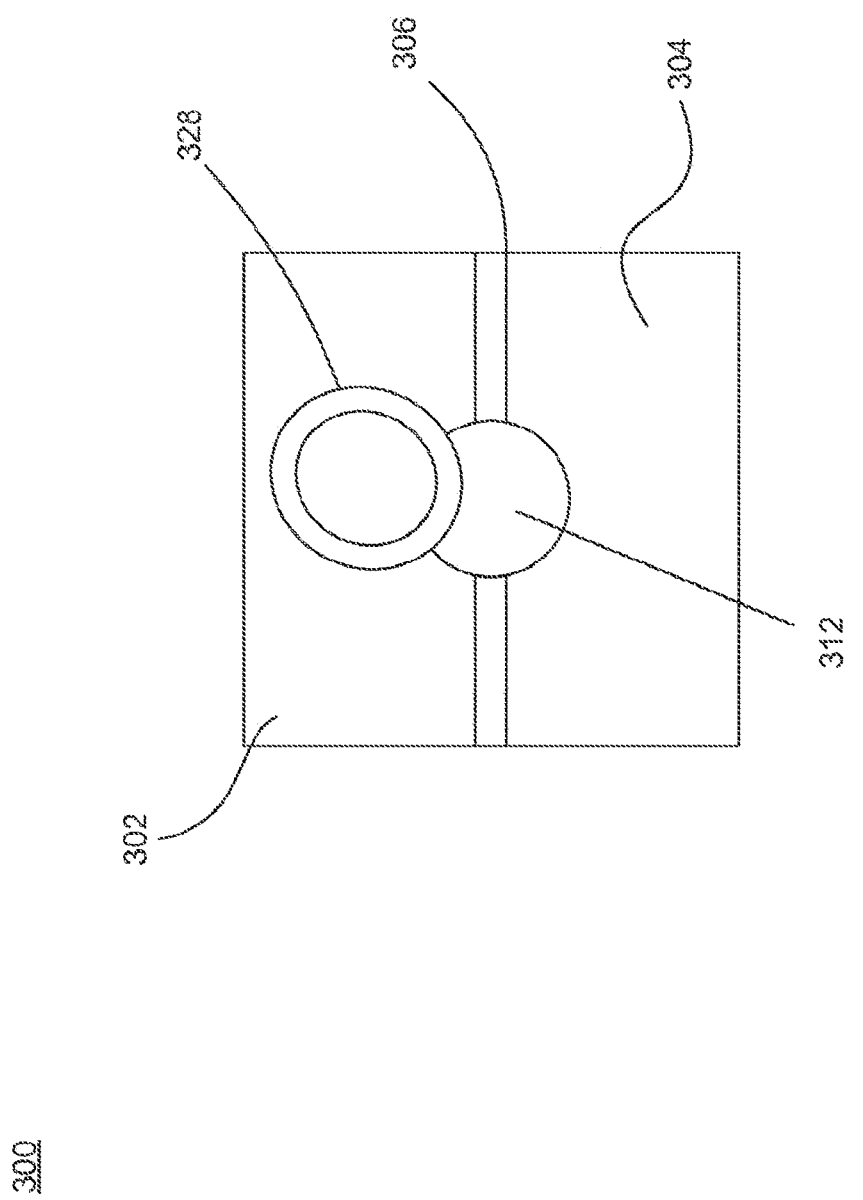

OBLIQUE EXPANDING FUSION CAGE DEVICE AND METHOD

CROSS-REFERENCE TO RELATED APPLICATIONS

This is a continuation of U.S. application Ser. No. 15/911,674 filed Mar. 5, 2018 and entitled Oblique Expanding Fusion Cage Device and Method, which will issue as U.S. Pat. No. 10,369,012 on Aug. 6, 2019, which is a continuation of U.S. application Ser. No. 14/442,974 filed May 14, 2015 and entitled Oblique Expanding Fusion Cage Device and Method, which issued as U.S. Pat. No. 9,907,671 on Mar. 6, 2018, which is a 371 U.S. National Stage of International Application No. PCT/US2013/070427, filed Nov. 15, 2013 and entitled Oblique Expanding Fusion Cage Device and Method, which claims the benefit of and priority to U.S. provisional application No. 61/727,504, filed Nov. 16, 2012 and entitled Oblique Expanding Fusion Cage Device and Method. The entire disclosures of each of the above applications are incorporated herein by reference.

TECHNICAL FIELD

The present application relates generally to general surgery and orthopedic and neurosurgical implants used for insertion within a space between a patient's vertebrae. More specifically, but not exclusively, the present invention concerns oblique expanding fusion cage devices implanted in the spine to maintain or re-establish proper spacing between a patient's vertebrae.

BACKGROUND

Fusion of the lumbar and thoracic spine currently involves implants and methods of maintaining or re-establishing the spacing within the spine. Many of the known implants do not accurately fit the interbody space and may result in decreased probability of fusion and cage migration.

SUMMARY

Various embodiments described herein relate to adjustable, oblique expanding fusion cage devices and methods that can maintain or re-establish anatomic spacing within a patient's spine.

In some embodiments, an oblique expanding fusion cage device including a body with a superior portion and an inferior portion is disclosed. The superior portion and the inferior portion have a proximal end and a distal end. The fusion cage device also includes a pathway, an opening, and an expanding member. The pathway travels from the proximal end to the distal end of the device between the superior and inferior portions. The opening in the proximal end of the body enables access to the pathway. The expanding member may be removably inserted into the opening and is moveable toward the distal end of the body, wherein the expanding member engages the superior portion and the inferior portion as the expanding member moves distally within the pathway.

In some embodiments, a surgical method for maintaining a vertebral interbody space in a spine of a patient is disclosed. The method includes the steps of obtaining a medical device and inserting the medical device into a patient through an opening in the skin. The medical device includes a body with a superior portion and an inferior portion. The superior portion and the inferior portion include a proximal end and a distal end. The fusion cage device also includes a pathway, an opening, and an expanding member. The pathway travels from the proximal end to the distal end of the device between the superior and inferior portions. The opening in the proximal end of the body enables access to the pathway. The expanding member may be removably inserted into the opening and is moveable toward the distal end of the body, wherein the expanding member engages the superior portion and the inferior portion as the expanding member moves distally within the pathway. The method also includes the steps of positioning the medical device in the vertebral interbody space and inserting the expanding member into the body of the medical device. Finally, the method includes the step of deploying the distal end of the medical device to engage two vertebrae adjacent to the vertebral interbody space.

These, and other objects, features and advantages of the embodiments described herein will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the device and methods described herein and together with the detailed description herein, serve to explain the principles devices and methods described herein. The drawings are only for purposes of illustrating preferred embodiments and are not to be construed as limiting.

FIG. 4 is a side view of two expanding members for the fusion cage device of FIG. 1, in accordance with various embodiments described herein;

FIG. 24 is a lateral view of an expanding member, in accordance with an various embodiments described herein;

FIG. 25 is a lateral view of an expanding member, in accordance with various embodiments described herein;

FIG. 26 is a lateral view of an expanding member, in accordance with various embodiments described herein;

FIG. 27 is a lateral view of an expanding member, in accordance with various embodiments described herein; and FIG. 28 is a proximal view of the fusion cage device of FIG. 21 with an alternative locking mechanism, in accordance with various embodiments described herein.

DETAILED DESCRIPTION

Figure 1:
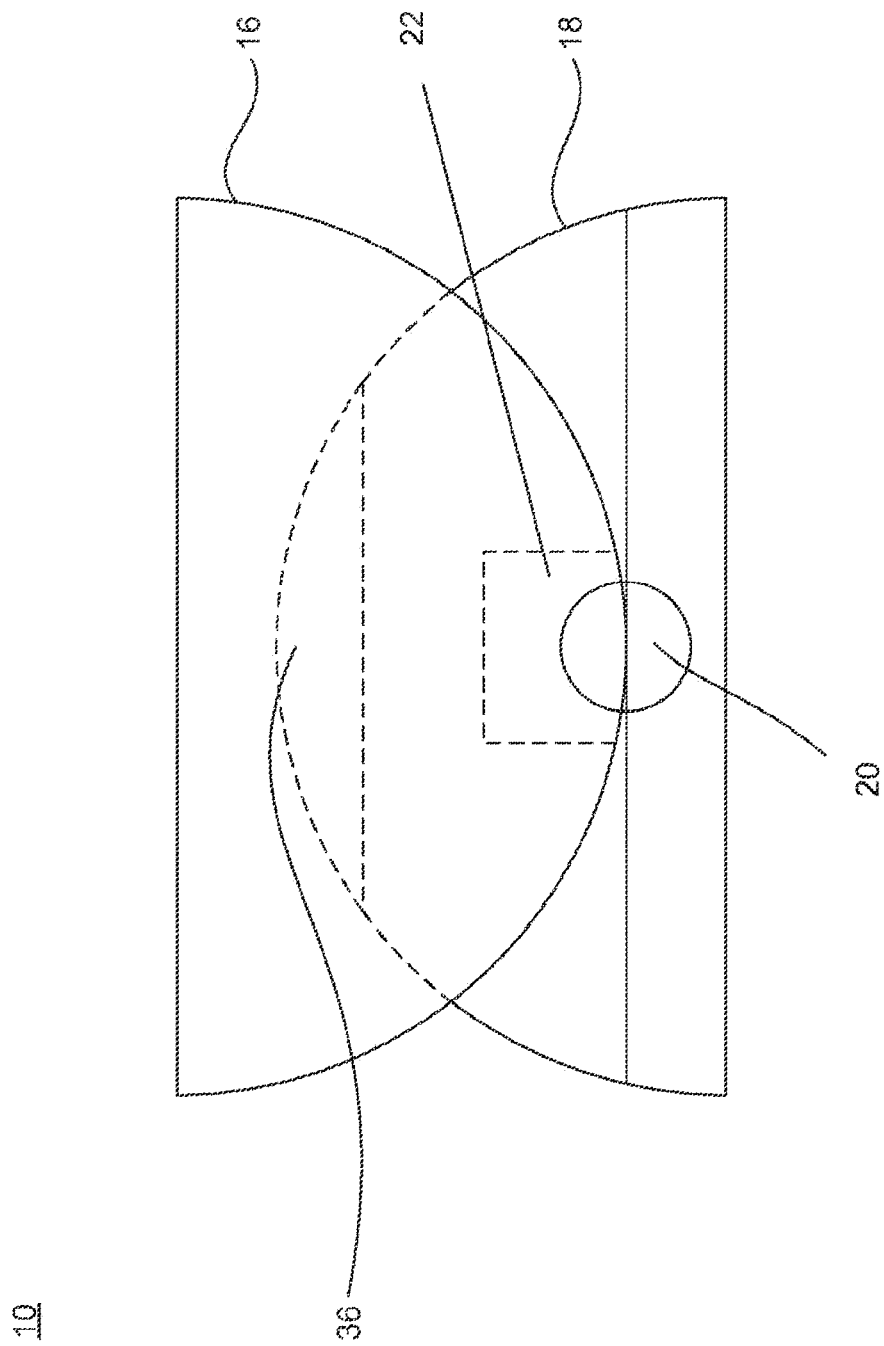
FIG. 1 is an end view of an obliquely expanding fusion cage device in an undeployed position, in accordance with various embodiments disclosed herein.
Figure 2:
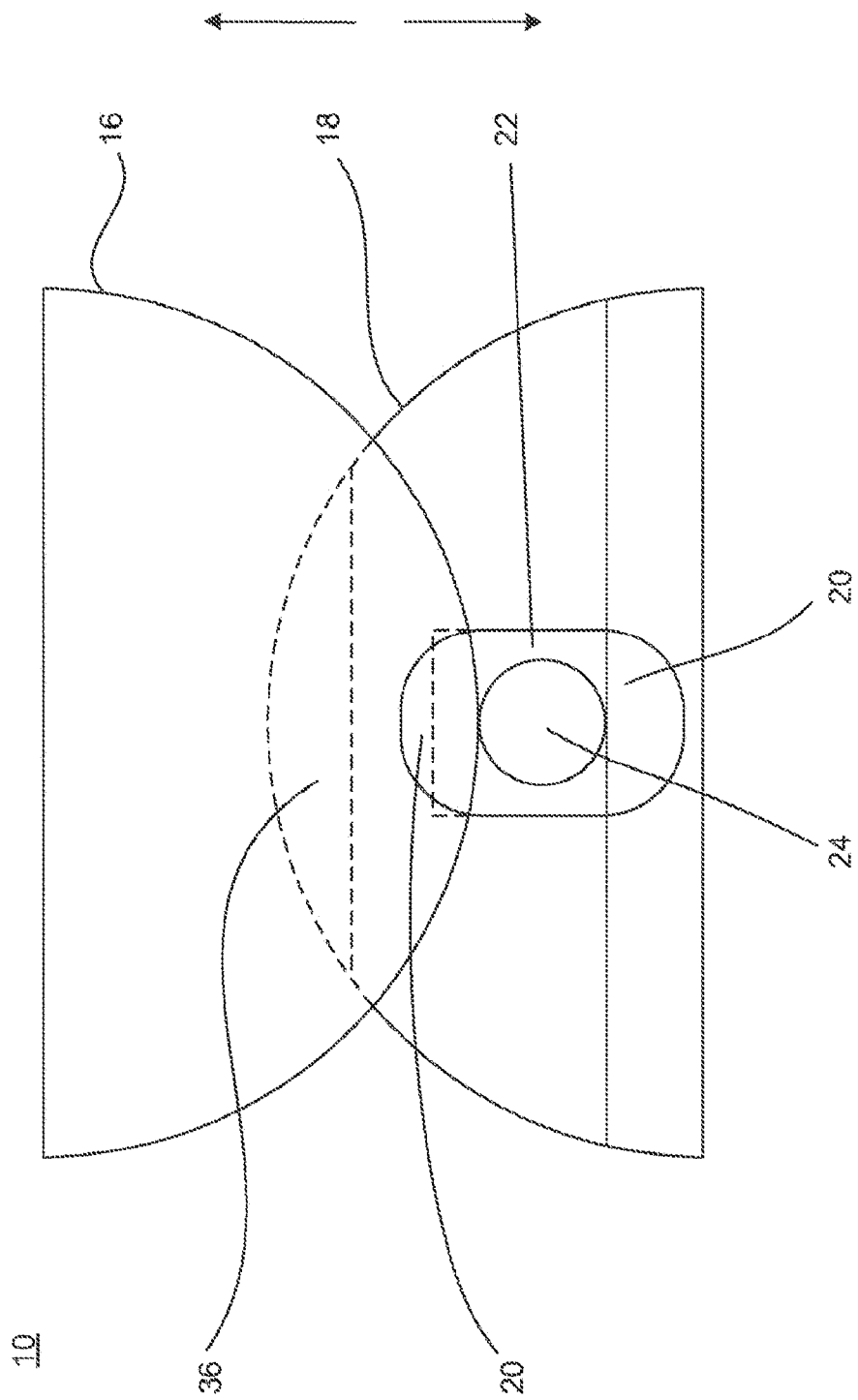
FIG. 2 is an end view of the fusion cage device of FIG. 1 in a deployed position, in accordance with various embodiments described herein.

Generally stated, disclosed herein are a number of embodiments of oblique expanding fusion cage devices. As used herein, the terms "obliquely expanding fusion cage device," "fusion cage device," "interbody fusion cage," "fusion cage," "device," and "cage implant" may be used interchangeably as they essentially describe the same type of device. Further, a surgical method for using the fusion cage devices to maintain a space between two vertebral bodies within a patient suffering from a diseased or damaged spinal column is discussed.

In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of an implant nearest the torso, while "distal" indicates the portion of the implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. In addition, for the purposes of this disclosure when referencing the device, the term "proximal" will mean the portion of the device closest or nearest the insertion instrument. The term "distal" shall mean the portion of the device farthest away from the insertion instrument.

Referring to the drawings, wherein like reference numerals are used to indicate like or analogous components throughout the several views, and with particular reference to FIGS. 1-5, there is illustrated an exemplary embodiment obliquely expanding fusion cage device 10. The fusion cage device 10 may have a generally rectangular or trapezoidal shape in the undeployed position to facilitate insertion into a patient's spine, although other shapes are possible. The fusion cage device 10 may also be narrower at a distal end 12 than at a proximal end 14 in the undeployed position for ease of insertion into the patient's spine. In the deployed position the fusion cage device 10 may have a generally trapezoidal shape to fill the interbody space. The fusion cage device 10 may include a superior portion 16 overlapping an inferior portion 18. The profile of the proximal and distal ends 14, 12, respectively, of the superior portion 16 and inferior portion 18 may be semi-circular halves fitted together and overlapping interiorly. The superior portion 16 may have a generally rectangular shaped lateral side with a plurality of openings 30 which include engagement teeth 32. The inferior portion 18 may have a generally rectangular shaped lateral side with a plurality of protrusions 34 which include engagement tabs 36 for engaging the engagement teeth 32 of the openings 30 in the superior portion 16.

Figure 3:
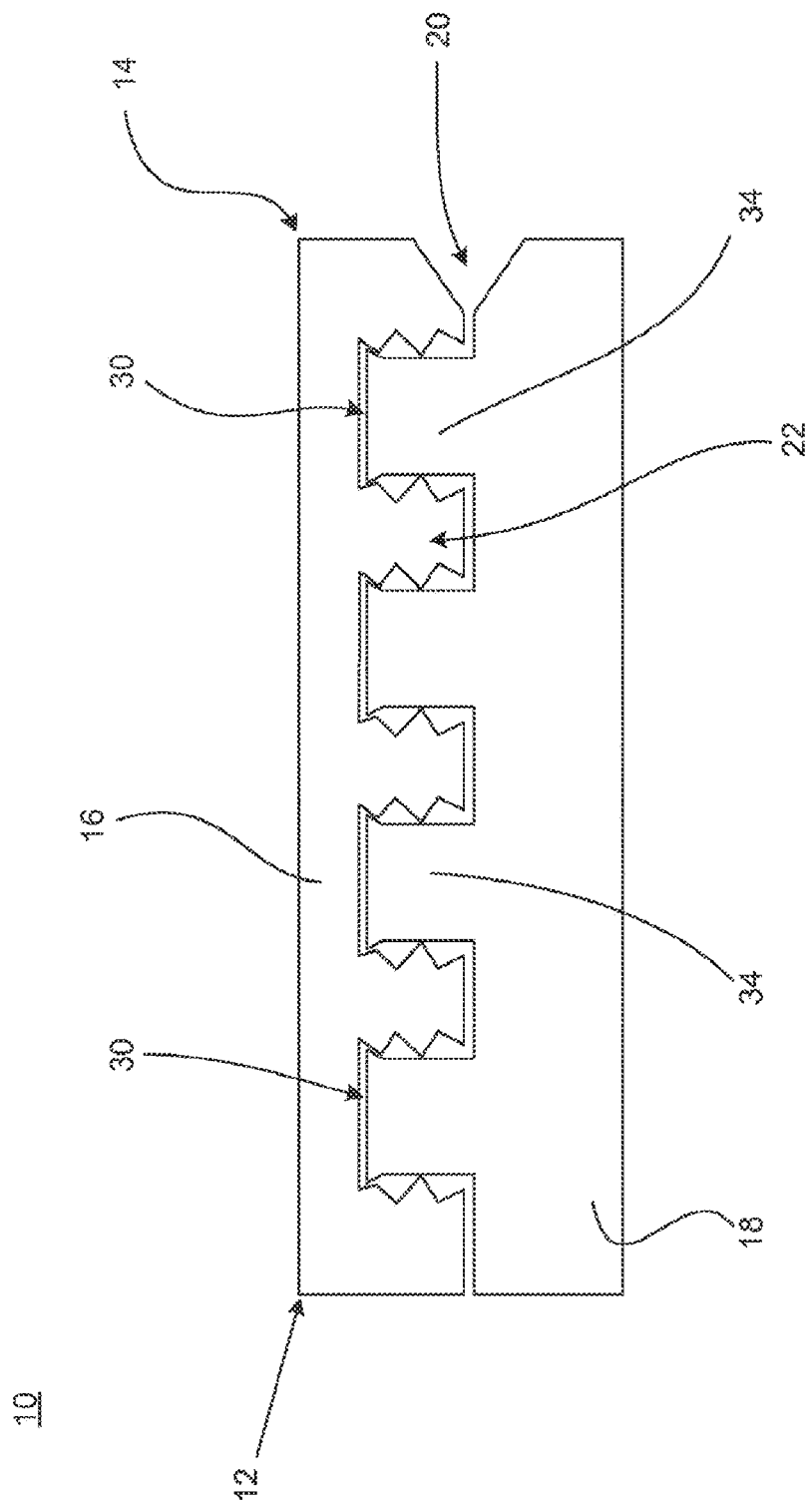
FIG. 3 is a side view of the fusion cage device of FIG. 1, in accordance with various embodiments described herein.
Figure 3A:
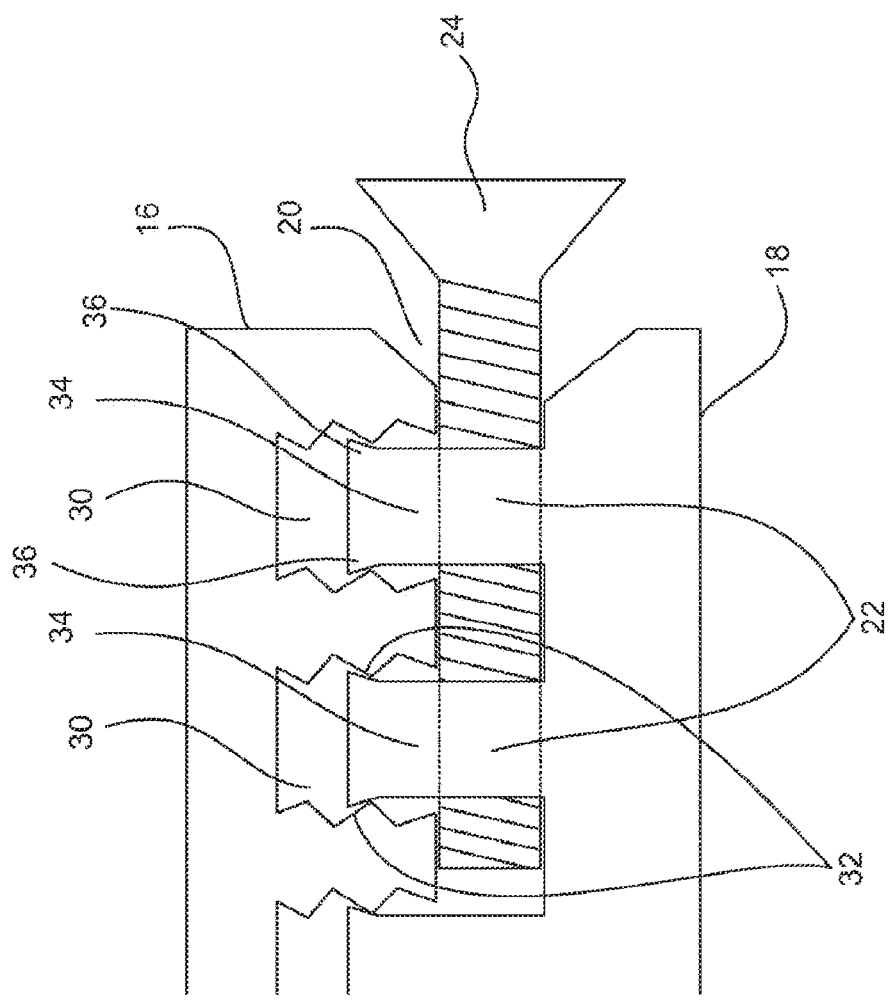
FIG. 3A is a side view of the fusion cage device of FIG. 1, in accordance with various embodiments described herein.
Figure 5:
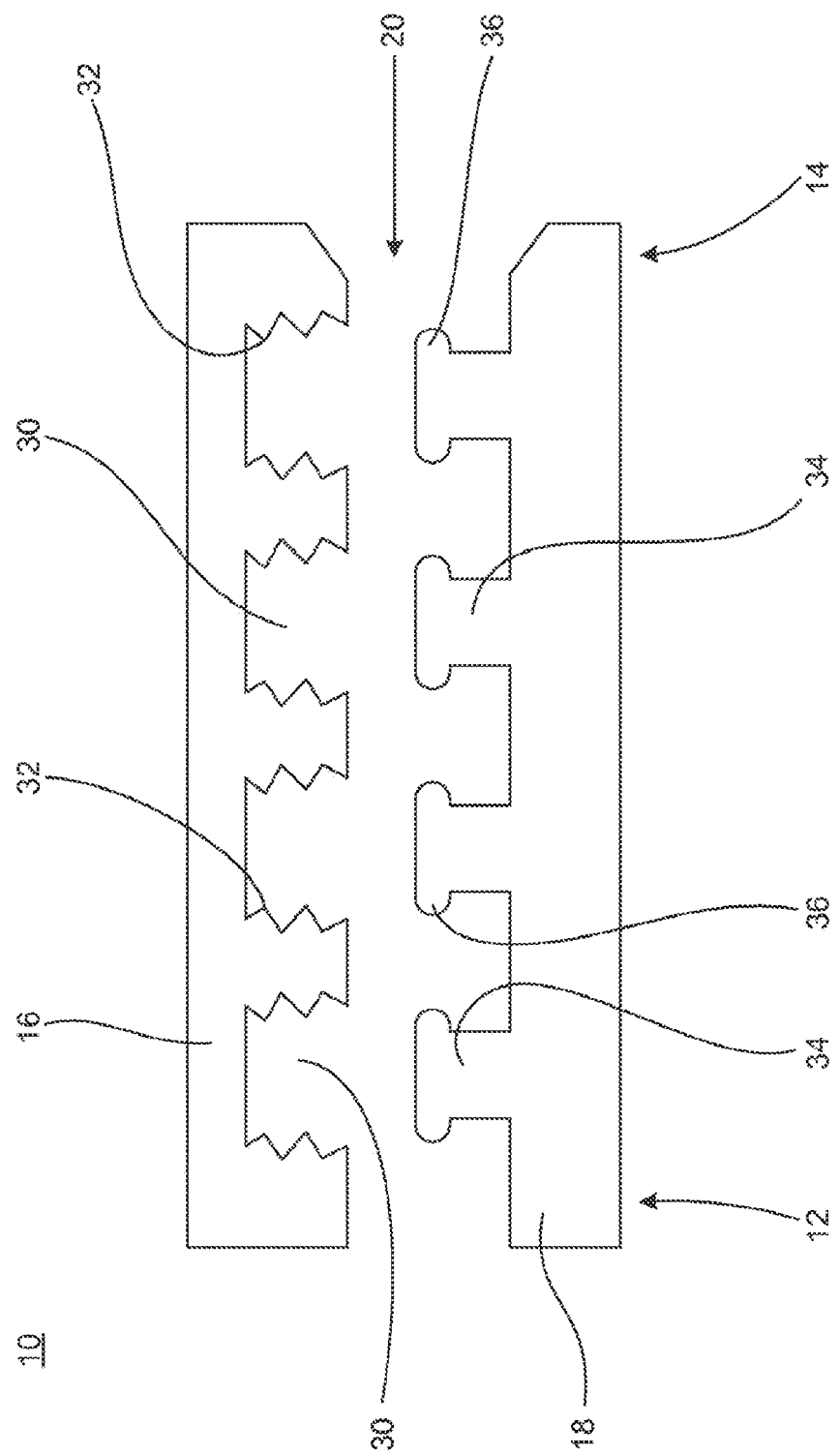
FIG. 5 is an exploded side view of the fusion cage device of FIG. 1, in accordance with various embodiments described herein.

The proximal end 14 may also include an opening 20 mating with a channel 22. As best shown in FIGS. 3, 3A and 5, the opening 20 may be comprised of slanted portions in both the superior portion 16 and the inferior portion 18. The slanted portions are slant inwardly and medially (i.e., towards the center of the device 10). The inwardly slanted portions in the superior and inferior portions 16, 18 may each have a semi-circular shape when viewed from the proximal end 14 (see, e.g., FIGS. 1 and 2) such that when the device 10 is in the undeployed position, the two slanted portions come together to form an opening 20 having a cone-shaped depression that can funnel an expanding member towards the channel 22.

The channel 22 is generally formed in the inferior portion 18. As shown in, for example, FIG. 3A, the channel 22 is generally made up of a series of aligned passages that extend through each of the protrusions 34 in the inferior portion 18. The shape of the channel 22 is generally not limited. As shown in, for example, FIGS. 1 and 2, the channel 22 has a square cross-sectional shape. Other shapes, such as a circular shape, can be used. The cross-sectional dimensions of the channel 22 are not limited, but are generally selected to accommodate expanding members with a variety of diameters. Generally speaking, the diameter of the expanding member will dictate how far the superior portion 16 can be moved away from the inferior portion 18 in a deployed position. As a result, the cross sectional dimensions of the channel 22 should be at least equal to the desired maximum distance of separation between the superior portion 16 and the inferior portion 18. The channel 22 may be uniform or narrow as it travels from the opening 20 at the proximal end 14 of the device 10 to the distal end 12. The opening 20 and channel 22 may be generally centered in a medial-lateral direction on the device 10.

An expanding member 24 may be inserted into the opening 20 and moved distally along the channel 22. As the expanding member 24 moves into the device 10, the expanding member 24 engages the superior portion 16 and the inferior portion 18 and moves the superior portion 16 away from the inferior portion 18 such that the device 10 fills the patient's intervertebral body space. As the expanding member 24 expands the cage device 10 the engagement tabs 36 move distally in the openings 30 and the tabs 36 are forced past the teeth 32 as the cage device 10 expands. The device 10 with an expanding member 24 inserted into the channel 22 is shown in FIG. 3A.

The expanding member 24 may be a screw or the like. The expanding member 24 may come in multiple sizes to provide varying amounts of expansion of the cage device 10. The expanding member 24 with a smaller diameter threaded shaft 26 will expand the cage device 10 less than an expanding member 24 with a larger diameter threaded shaft 28.

Figure 6:
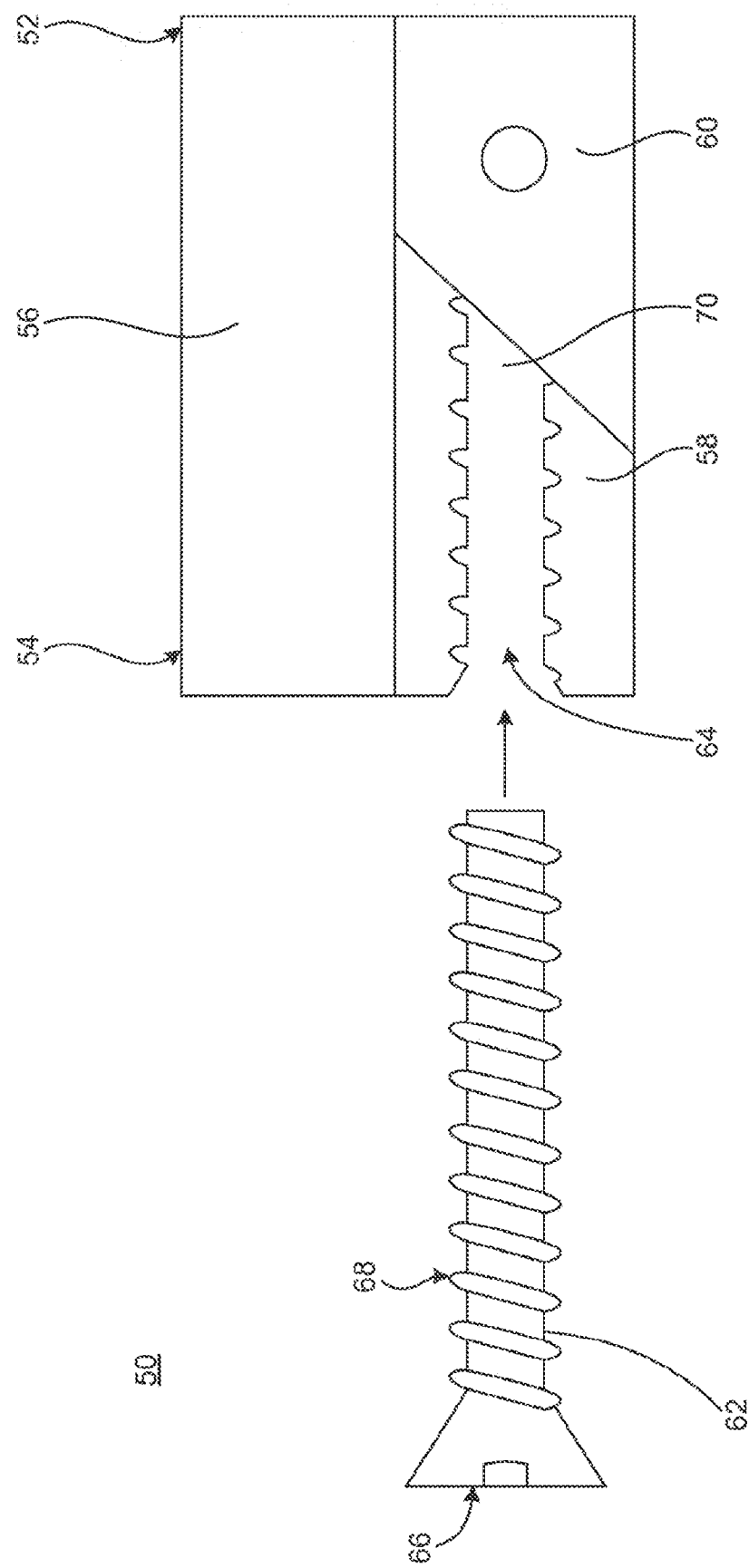
FIG. 6 is a lateral view of a fusion cage device and an expanding member, in accordance with various embodiments described herein.
Figure 7:
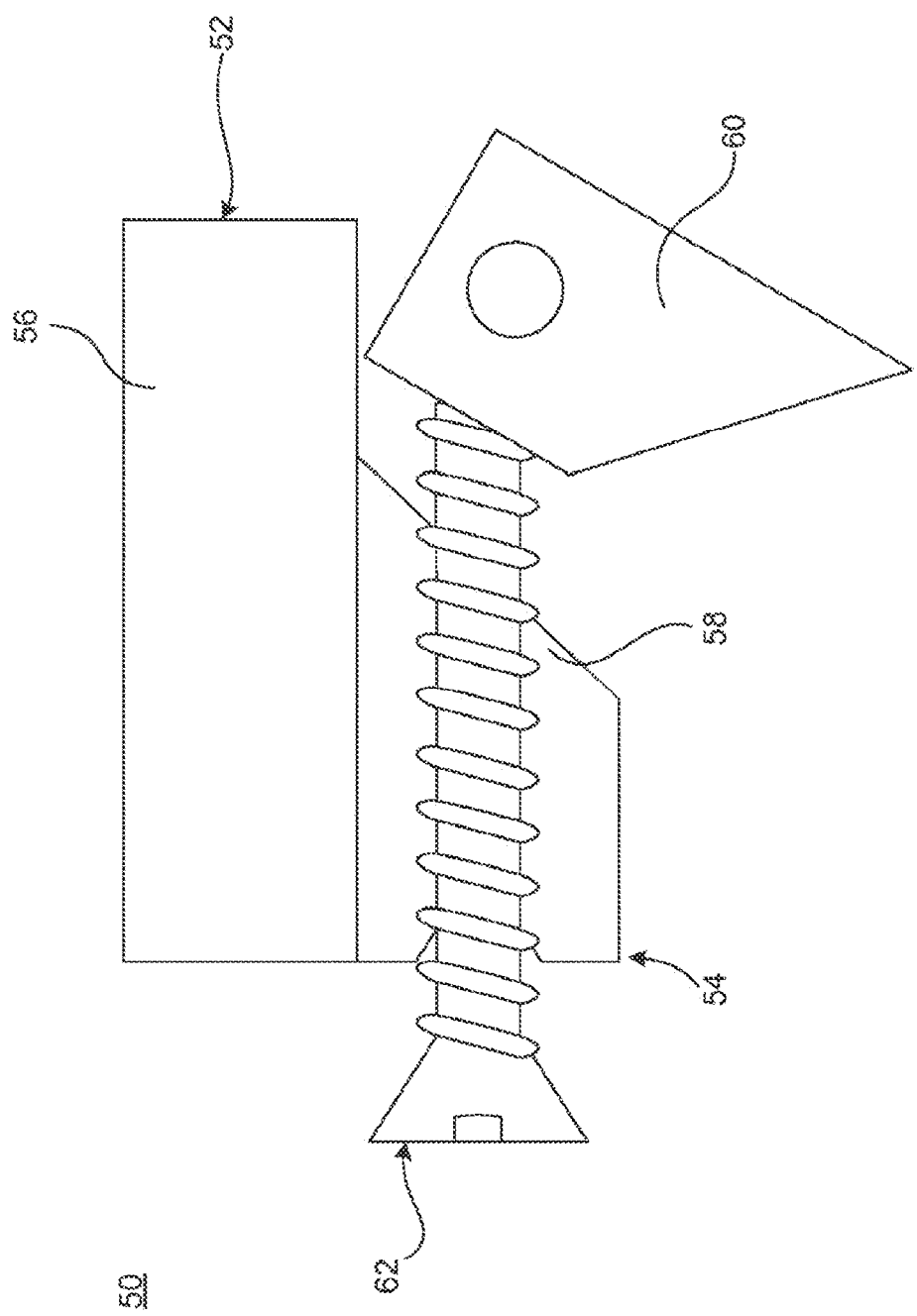
FIG. 7 is a lateral view of the fusion cage device of FIG. 6 with the expanding member partially inserted into an inferior portion of the fusion cage device, in accordance with various embodiments described herein.
Figure 8:
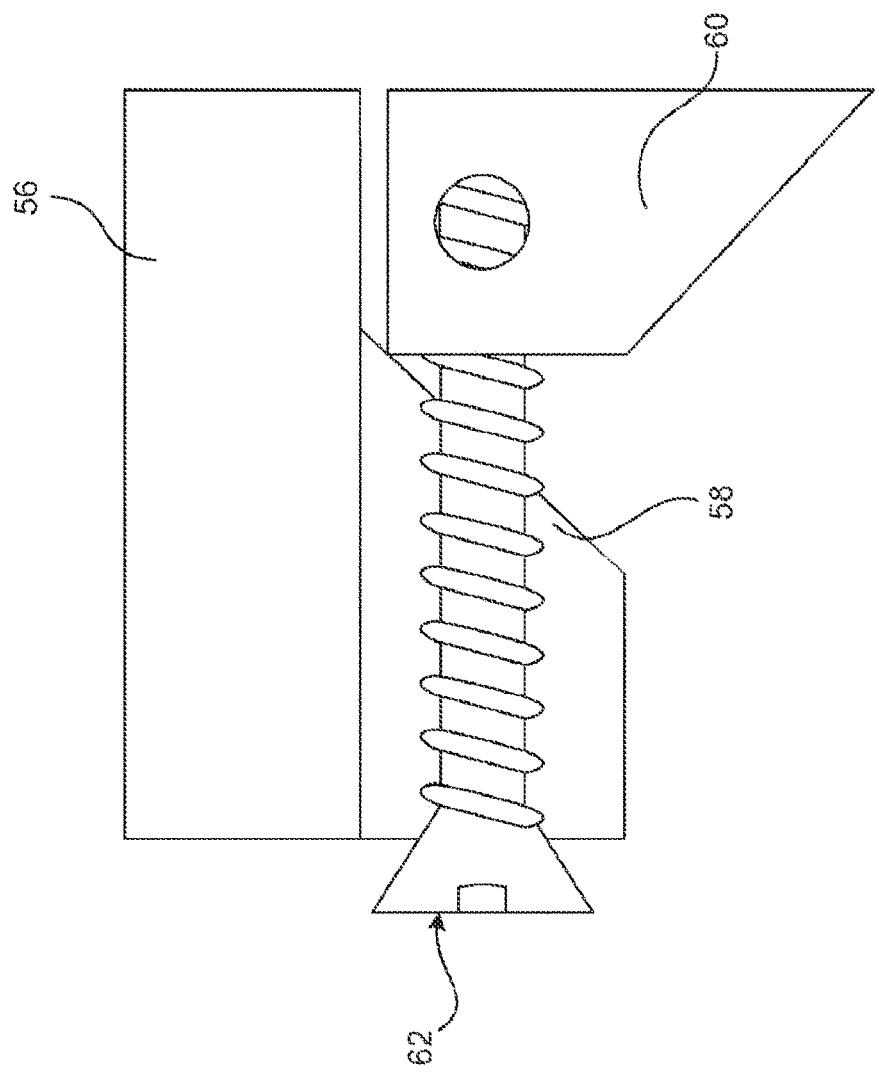
FIG. 8 is a lateral view of the fusion cage device of FIG. 6 with the expanding member fully inserted into the inferior portion of the fusion cage device, in accordance with various embodiments described herein.

FIGS. 6-8 show various embodiments of a fusion cage device 50. In an undeployed position the fusion cage device 50 may have a rectangular or trapezoidal shape to facilitate insertion between two vertebrae of a patient. In addition, for ease of insertion, the distal end 52 of the device 50 may be narrower than the proximal end 54 of the device 50 in an undeployed position. In a deployed position the fusion cage device 50 may have a generally trapezoidal shape as the device 50 deploys to fill the space between two vertebrae. The fusion cage device 50 may include a superior portion 56 adjacent an inferior portion 58 and a deployment portion 60. The deployment portion 60 can be generally parallel to the superior portion 56 in an undeployed position and generally perpendicular to the superior portion 56 when deployed. The deployment portion 60 may be hinged to the superior portion 56, enabling the deployment portion 60 to swing open as it is engaged by an expanding member 62. Alternatively, the deployment portion 60 may be hinged to the inferior portion 58 enabling the deployment portion 60 to swing open as it is engaged by the expanding member 62.

An expanding member 62 may be inserted into an opening 64 in the proximal end 54 of the device 50 to engage the inferior portion 58 and the deployment portion 60. The expanding member 62 may be a screw which includes a drive head 66 and a threaded shaft 68. As the expanding member 62 is moved from the proximal end 54 to the distal end 52 of the device 50 the deployment portion 60 is pushed from a generally parallel position, as seen in FIG. 6, to a partially deployed position, as seen in FIG. 7, and finally reaches a fully deployed position, as shown in FIG. 8, wherein the deployment portion 60 is generally perpendicular to the superior portion 56. The inferior portion 58 may include a threaded channel 70 wherein the threads of the threaded channel 70 correspond with the threads on the expanding member 62. When the expanding member 62 is fully inserted into the device 50, the deployment portion 60 will be in a fully deployed position generally perpendicular to the superior portion 56. As the deployment portion 60 is deployed, it extends the distal end 52 of the device 50 and in turn distracts the distal portion of the intervertebral space.

Figure 9:
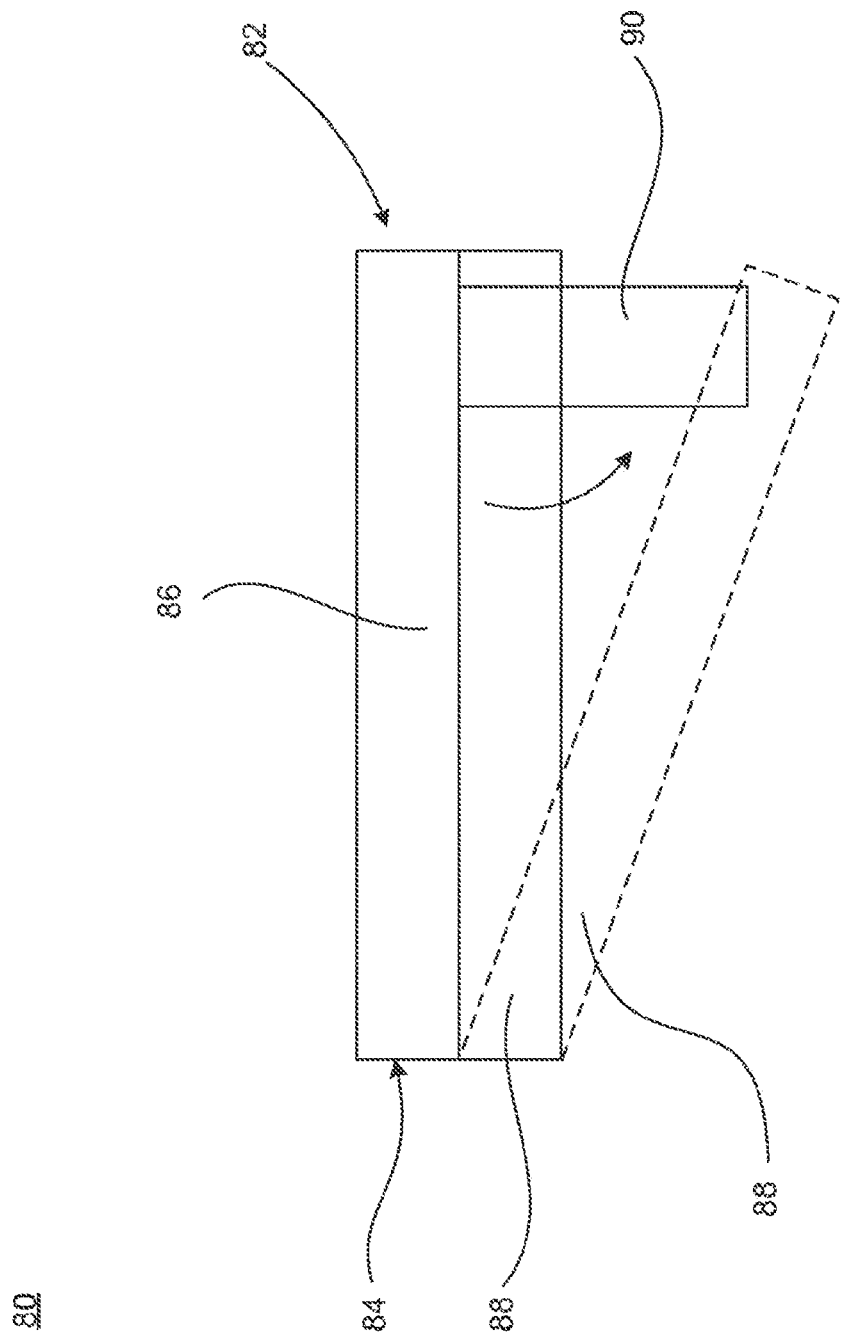
FIG. 9 is a lateral view of a fusion cage device with an expanding member, in accordance with various embodiments described herein.

FIG. 9 shows various embodiments of a fusion cage device 80. In an undeployed position the fusion cage device 80 may have a rectangular or trapezoidal shape to facilitate insertion between two vertebrae of a patient. In addition, a distal end 82 of the device 80 may be narrower than a proximal end 84 of the device 80 in an undeployed position. In a deployed position the fusion cage device 80 may have a generally trapezoidal shape as the device 80 deploys to fill the space between two vertebrae. The fusion cage device 80 may include a superior portion 86 adjacent an inferior portion 88 and a deployment portion 90. The deployment portion 90 is generally parallel to the superior portion 86 in an undeployed position and generally perpendicular to the superior portion 86 when deployed. A deployment mechanism (not shown) may be inserted into an opening in the proximal end 84 of the device 80 to engage the superior portion 86, inferior portion 88, and deployment portion 90. The deployment mechanism may be a screw or the like, such as described above with reference to FIGS. 6-8. As the deployment mechanism is moved from the proximal end 84 to the distal end 82 of the device 80 the deployment portion 90 is pushed from a parallel position to a perpendicular deployed position as shown in FIG. 9. In some embodiments, the deployment portion 90 can be hingedly coupled at one end with distal end 82 of the superior portion 86 so that the deployment portion 90 can hinge between a undeployed configuration and a deployed configuration. When the deployment mechanism has been fully inserted into the device 80, the deployment portion 90 will be in a fully deployed position generally perpendicular to the superior portion 86. In addition, as the deployment mechanism is advanced toward the distal end 82 of the device 80, the inferior portion 88 may deploy distally. As the inferior portion 88 and the deployment portion 90 are deployed they distract the distal end 82 of the device 80 and in turn distract the distal portion of the intervertebral space.

Figure 10:
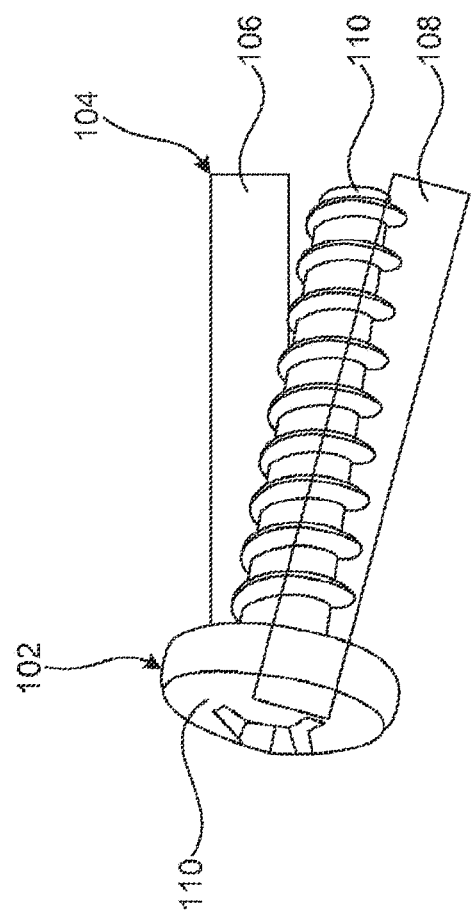
FIG. 10 is a lateral view of a fusion cage device, in accordance with various embodiments described herein.
Figure 11:
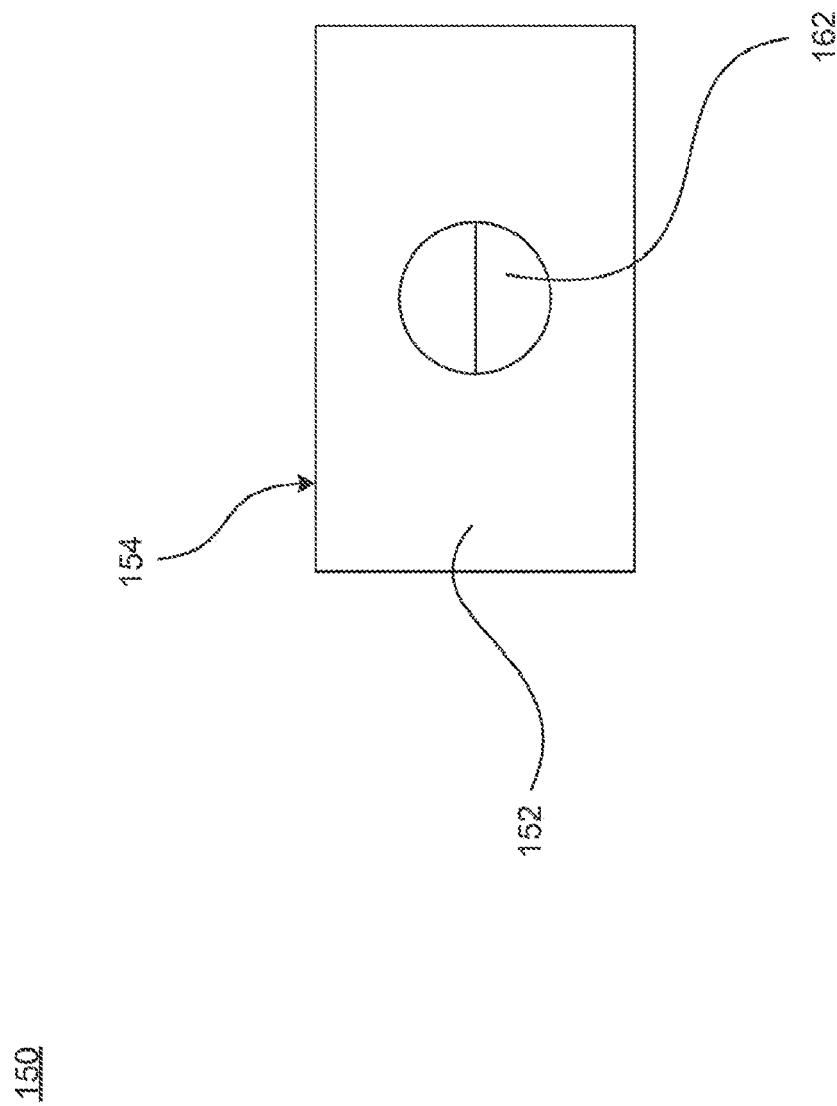
FIG. 11 is a proximal view of a fusion cage device, in accordance with various embodiments described herein.
Figure 12:
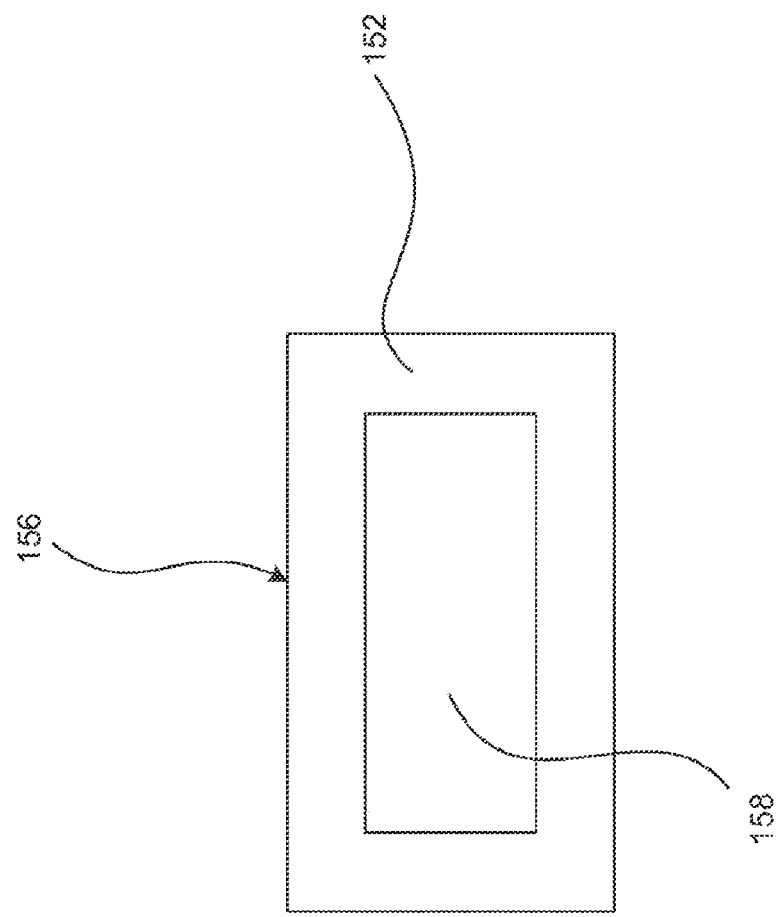
FIG. 12 is a distal view of the fusion cage device of FIG. 11, in accordance with various embodiments described herein.
Figure 13:
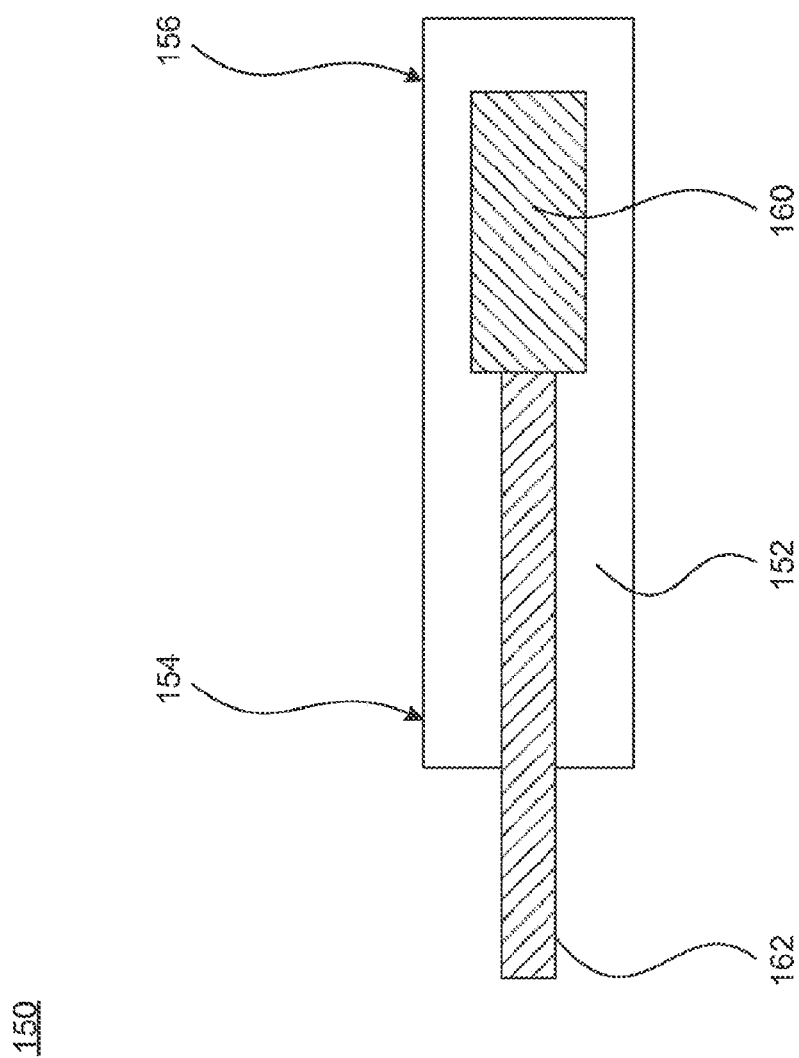
FIG. 13 is a lateral cross-sectional view of the fusion cage device of FIGS. 11 and 12 in an undeployed position, in accordance with various embodiments described herein.
Figure 14:
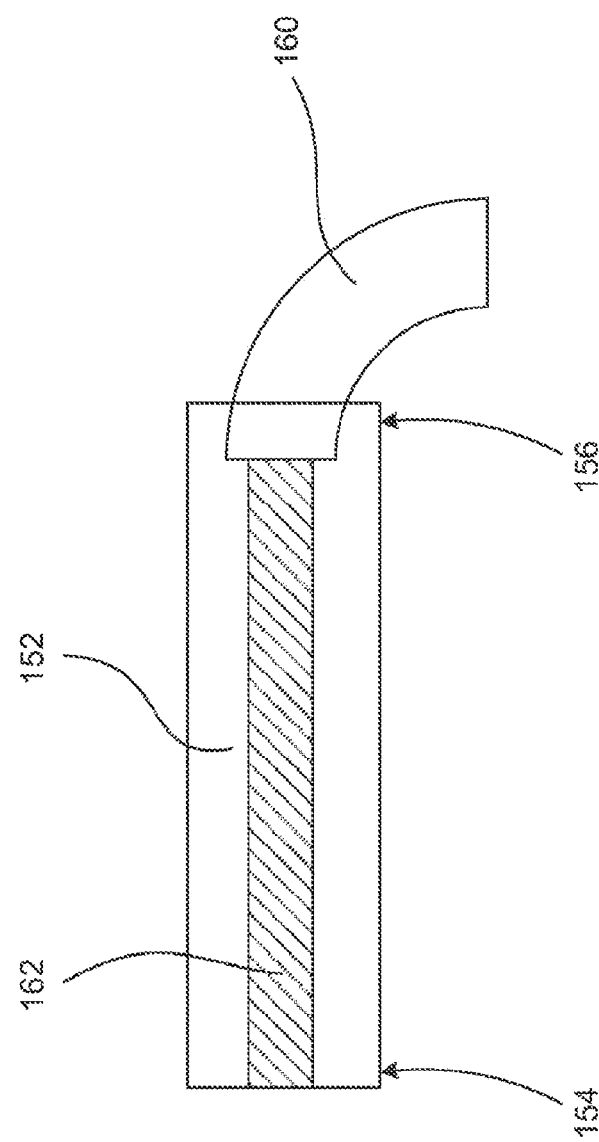
FIG. 14 is a lateral cross-sectional view of the fusion cage device of FIGS. 11-13 in a deployed position, in accordance with various embodiments described herein.
Figure 15:
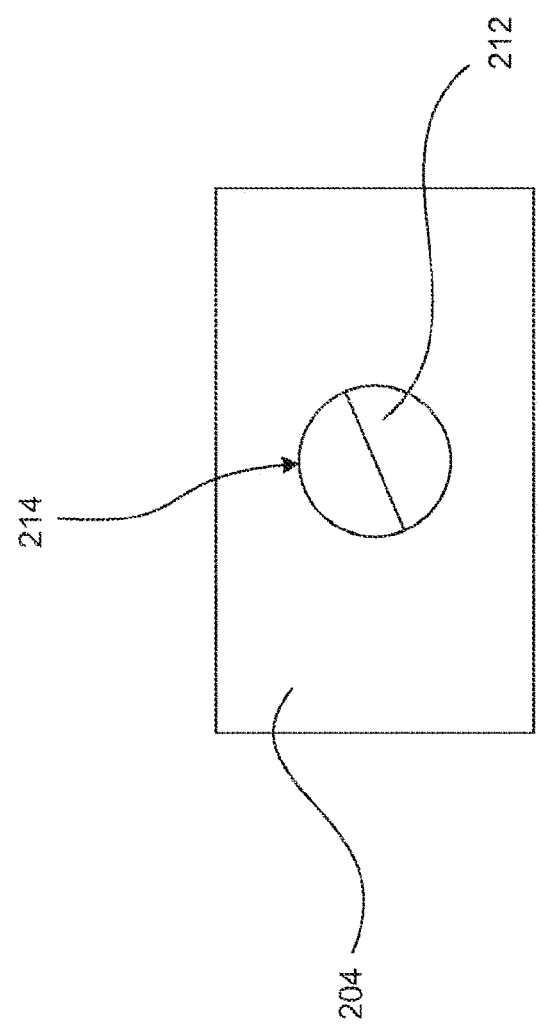
FIG. 15 is a proximal view of a fusion cage device, in accordance with various embodiments described herein.
Figure 16:
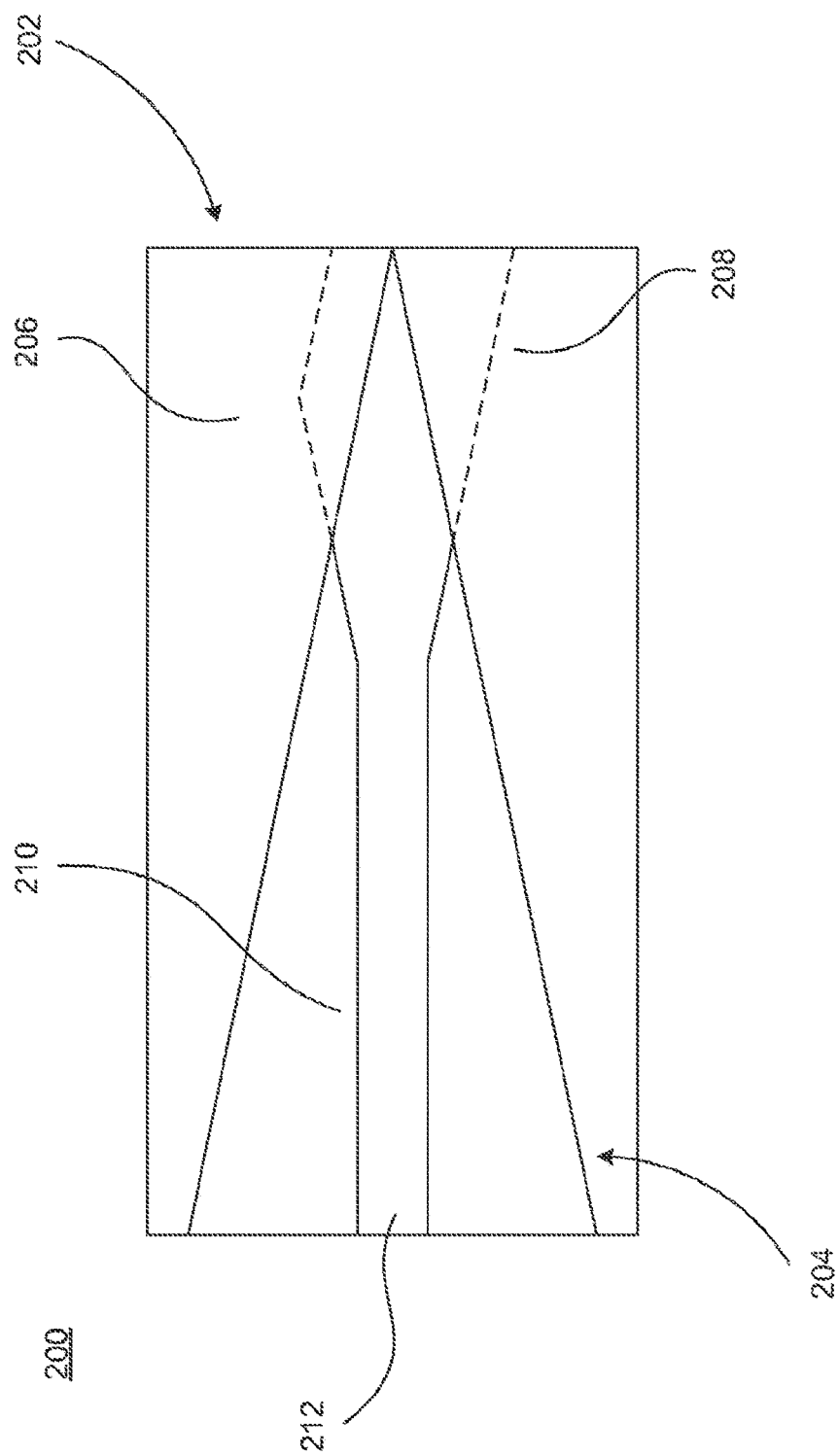
FIG. 16 is a lateral cross-sectional view of the fusion cage device of FIG. 15, in accordance with various embodiments described herein.

FIG. 10 illustrates various embodiments of an obliquely expanding fusion cage device 100 including a proximal end 102 and a distal end 104. The undeployed fusion cage device 100 may have a rectangular or trapezoidal shape to facilitate insertion into the patient's spine. To help facilitate the insertion of the device 100 into a patient's spine the distal end 104 may also be narrower than the proximal end 102 of the device 100 in the undeployed position. The fusion cage device 100 may have a trapezoidal shape in the deployed position to fill or expand the intervertebral disc space. The fusion cage device 100 may include a superior portion 106 hingedly connected to an inferior portion 108 and an expanding member 110 for engaging the superior and inferior portions 106, 108, respectively. The superior portion 106 and inferior portion 108 may be hingedly connected at the proximal end 102. The superior portion 106 and the inferior portion 108 may also each have a relatively trapezoidal shape. The superior portion 106 and inferior portion 108 may each be larger at the distal end 104 than the proximal end 102. As the expanding member 110 is inserted into an opening in the proximal end 102 of the device 100 the expanding member 110 engages the interior surface of each of the superior portion 106 and the inferior portion 108. As the expanding member 110 is advanced toward the distal end 104 of the device 100 the superior portion 106 and inferior portion 108 are expanded away from each other to fill or expand the intervertebral disc space. The expanding member 110 may be a screw or similar expansion mechanism.

Referring now to FIGS. 11-14, various embodiments of an expanding fusion cage device 150 are illustrated. The fusion cage device 150 may be generally rectangular or trapezoidal in shape when undeployed. In addition, the distal end 156 may be narrower than the proximal end 154 to assist in insertion of the device 150 between two adjacent vertebrae. Once deployed the cage device 150 will likely have a distal end 156 that is wider than the proximal end 154. Fusion cage device 150 includes a body 152 with a proximal end 154 and a distal end 156. The body 152 may include a center opening 158 for receiving a curved shim 160 which may be attached to an expanding member 162. The curved shim 160 may be made of a variety of biocompatible materials, including, but not limited to, titanium, stainless steel, PEEK, or a memory metal, such as Nitinol. The expanding member 162 may be inserted into the opening 158 at the proximal end 154 of the body 152 to move the curved shim 160 toward the distal end 156. The expanding member 162 may be a screw which may be turned to advance the shim 160 along the opening 158 to the distal end 156. The expanding member 162 may include a threaded shaft which engages a threaded surface on the interior of the body 152 when inserted into the center opening 158. When the shim 160 reaches the distal end 156 of the body 152 it may exit the opening 158 at the distal end 156 and curve to contact a cephalad or caudal endplate when completely deployed. The cephalad or caudal endplate is displaced distally as the shim 160 pushes against the endplate.

Figure 17:
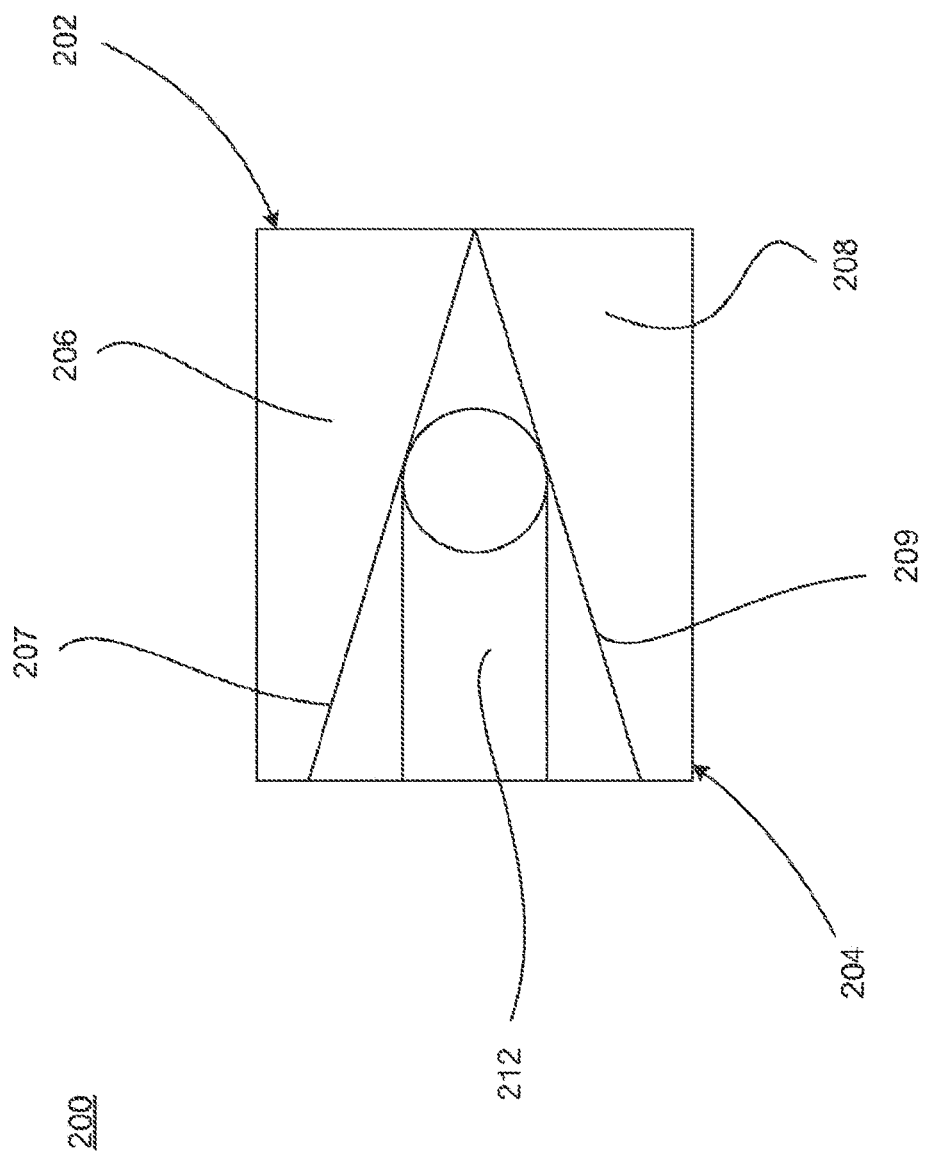
FIG. 17 is a lateral cross-section view of the fusion cage device of FIGS. 15 and 16 in an undeployed position with the expanding member partially inserted, in accordance with various embodiments described herein.
Figure 18:
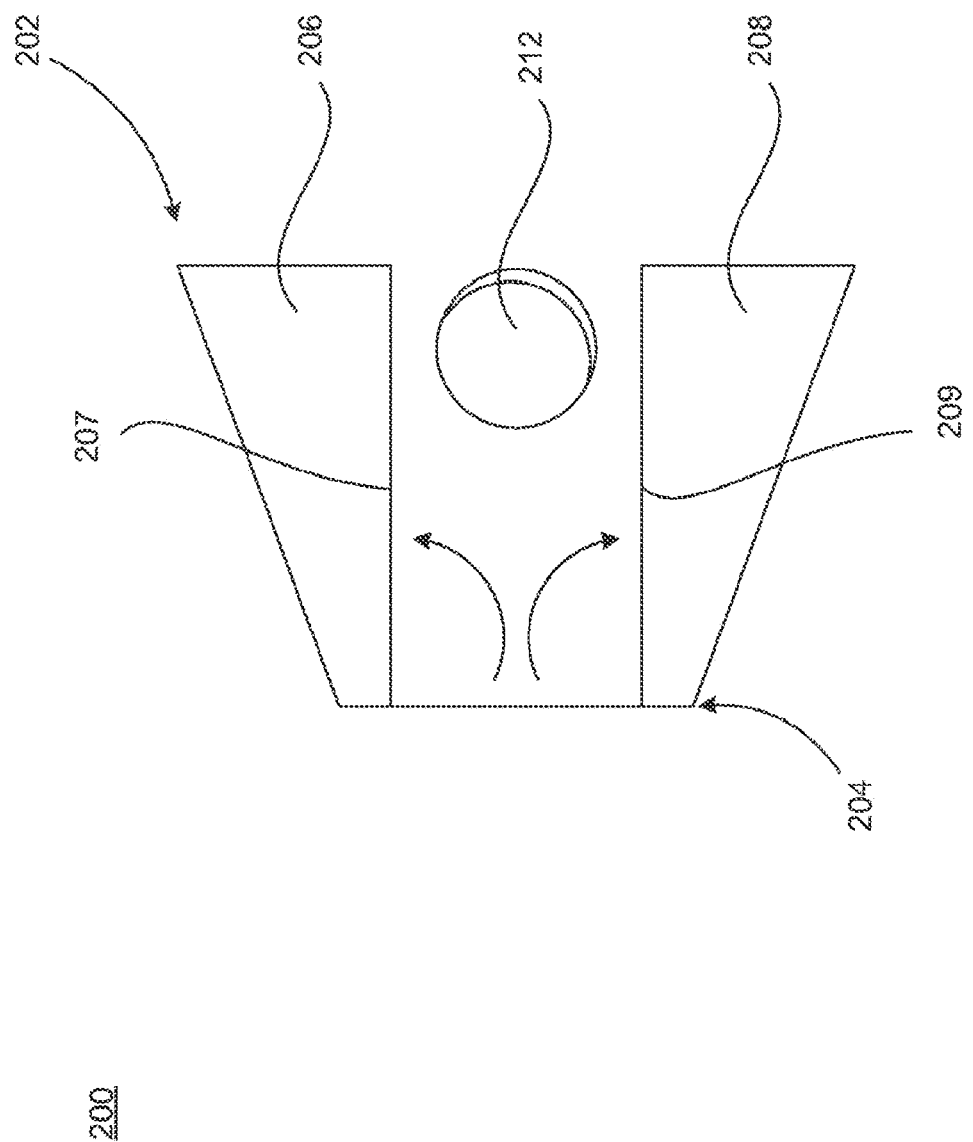
FIG. 18 is a lateral cross-section view of the fusion cage device of FIGS. 15-17 in a deployed position with the expanding member fully inserted, in accordance with various embodiments described herein.

Various embodiments of an expanding fusion cage device 200 are illustrated in FIGS. 15-18. The fusion cage device 200 may have a generally rectangular or trapezoidal shape in the undeployed position, as illustrated in FIG. 17, to facilitate insertion between two vertebrae. In addition, in the undeployed position the fusion cage device 200 may be narrower at a distal end 202 than a proximal end 204. In the deployed position, shown in FIG. 18, the fusion cage device 200 will have a generally trapezoidal shape to fill the interbody space and enable fusion between the two vertebrae. The fusion cage device 200 may include a superior portion 206 adjacent an inferior portion 208 which in an undeployed position creates an opening 210. The opening 210 may be tapered from the proximal end 204 to the distal end 202 for mating with an expanding member 212. As the opening 210 tapers toward the distal end 202 it may narrow to be much smaller than the width of the expanding member 212. The opening 210 may be accessed at the proximal end 204 through a hole 214. The hole 214 may be nearly identical to the size of the expanding member 212. The expanding member 212 may be a screw, sliding member, or like expansion mechanism. A screw-like expanding member 212 may include a threaded end. As the expanding member 212 is inserted into the opening 210 it interacts with the interior surfaces 207, 209 of the superior portion 206 and the inferior portion 208 forcing the superior portion 206 and the inferior portion 208 to separate. In some embodiments, the superior portion 206 and the inferior portion 208 each about their proximal end 204 when being separated such that the interior surfaces 207, 209 go from an angled orientation in the undeployed state to a generally parallel orientation in the deployed state.

If a screw-like expanding member 212 is used the interior surfaces 207, 209 of the distal end 202 of the superior and inferior portions 206, 208 may be threaded to mate with a corresponding threaded portion of the expanding member 212. Alternatively, if a sliding type expanding member 212 is used the sliding type member 212 may be pushed into the interior surfaces 207, 209 of the superior and inferior portions 206, 208 at the distal end 202 of the cage device 200 forcing the superior and inferior portions 206, 208 apart. In a fully deployed position the sliding type member 212 is fit into a locking mechanism (not shown) which secures the sliding type member 212 to the device 200. As the superior portion 206 and inferior portion 208 separate, the distal end 202 of the device 200 displaces both cephalad and caudally relative to the proximal end 204.

Figure 19:
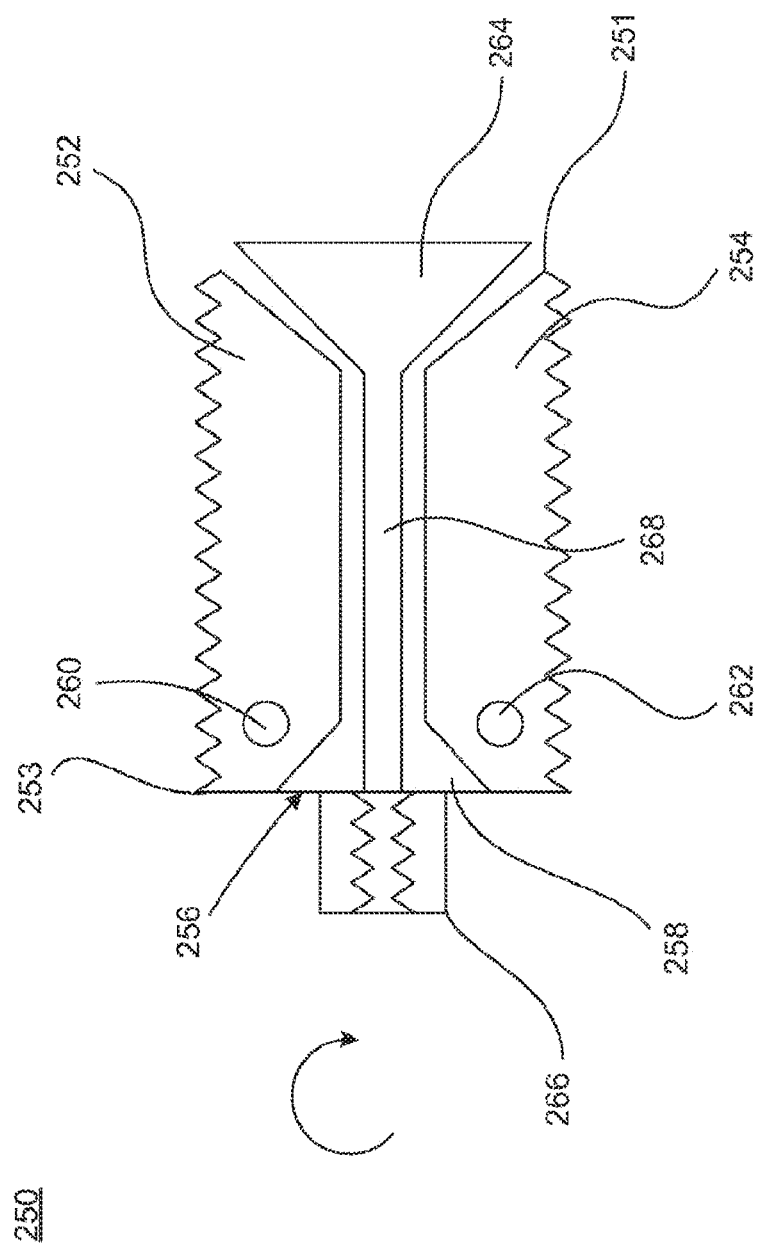
FIG. 19 is a lateral cross-sectional view of a fusion cage device in an undeployed position, in accordance with various embodiments described herein.
Figure 20:
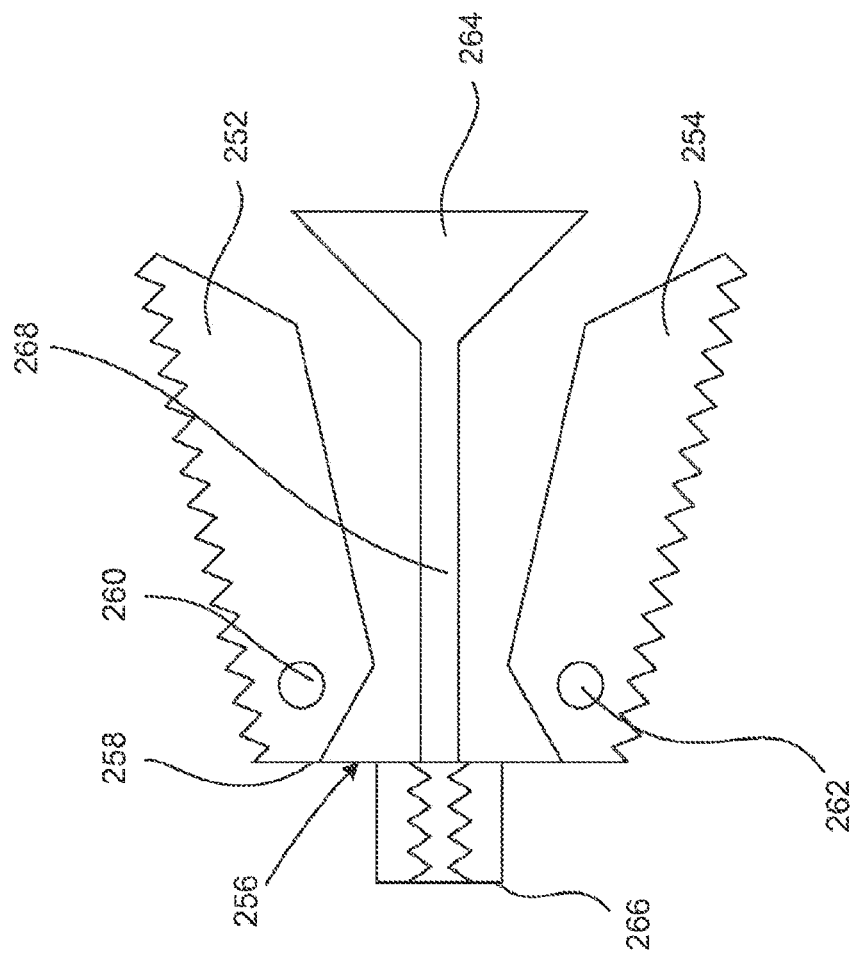
FIG. 20 is a lateral cross-section view of the fusion cage device of FIG. 19 in a partially deployed position, in accordance with various embodiments described herein.
Figure 21:
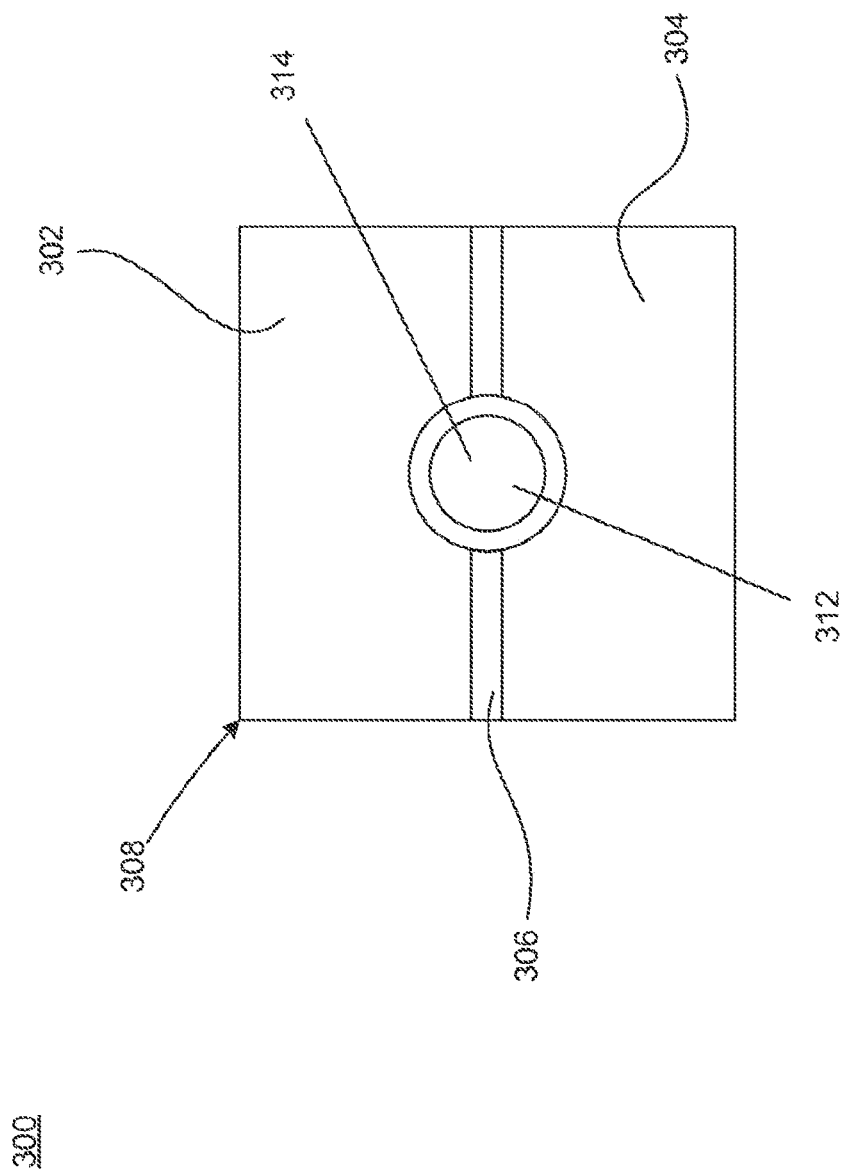
FIG. 21 is a proximal view of a fusion cage device, in accordance with various embodiments described herein.
Figure 22:
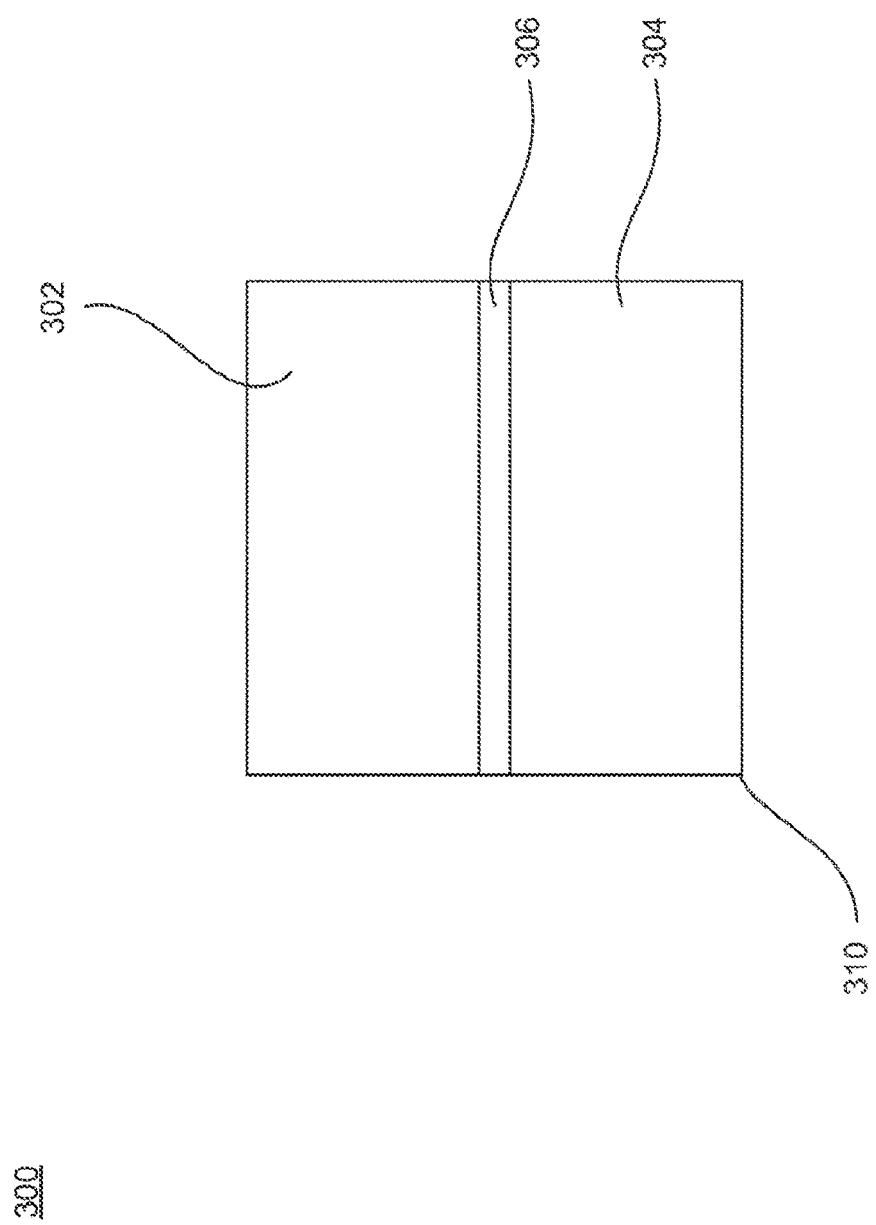
FIG. 22 is a distal view of the fusion cage device of FIG. 21, in accordance with various embodiments described herein.
Figure 23:
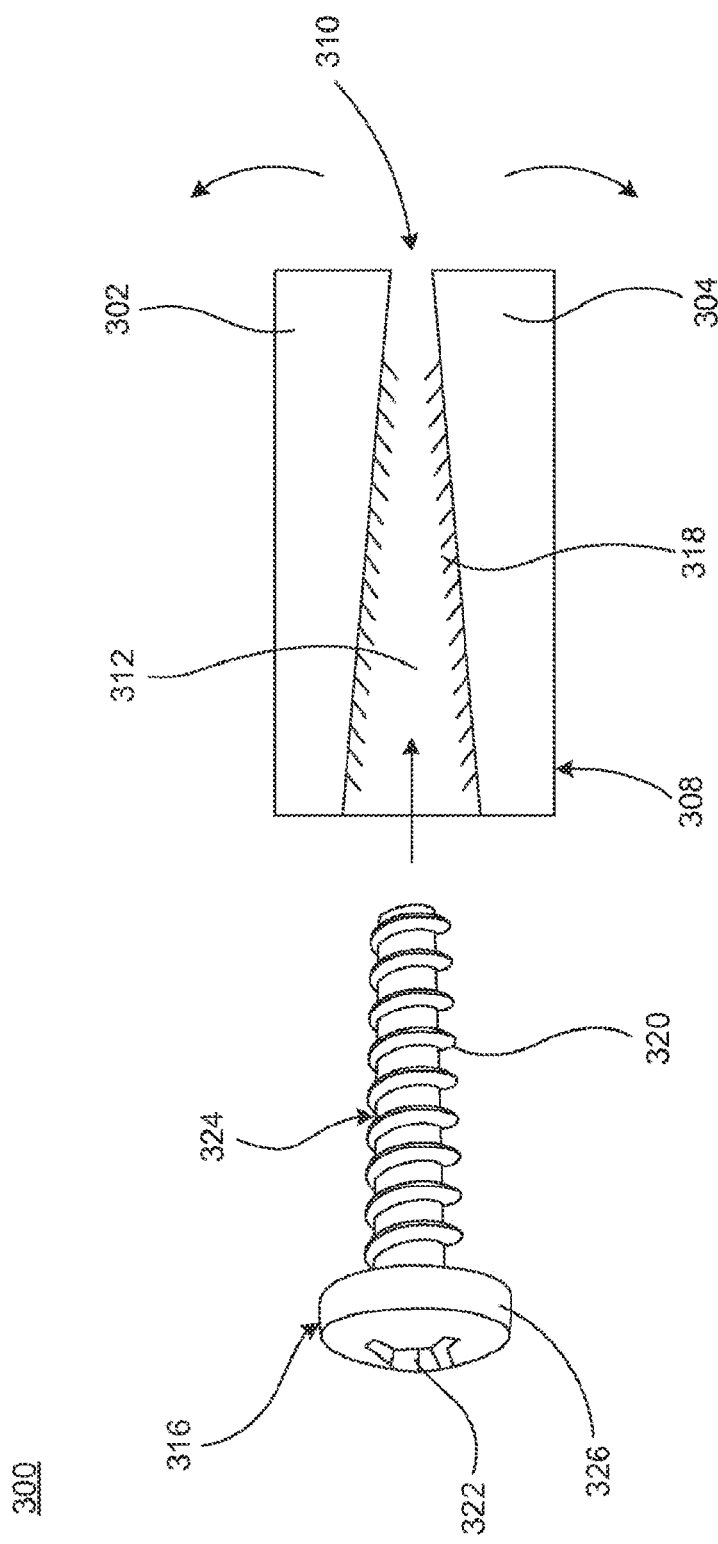
FIG. 23 is a partially exploded lateral cross-sectional view of the fusion cage device of FIGS. 14 and 15 with an expanding member being inserted into the fusion cage device, in accordance with various embodiments described herein.

Referring now to FIGS. 19 and 20, various embodiments of an expanding fusion cage device 250 are shown. The fusion cage device 250 includes a first arm 252 parallel to a second arm 254 and an expanding member 256. The expanding member 256 may include a body 258 at the proximal end 253 and a wedge 264 at the distal end 251. A winding mechanism 266 may be coupled to the body 258. The winding mechanism 266 and the wedge 264 may be connected by a cable 268. The cable 268 may run between and parallel to the first arm 252 and the second arm 254. The first arm 252 may be attached to the body 258 of the expanding member 256 with a pivot pin 260 and the second arm 254 may be attached to the body 258 of the expanding member 256 with a pivot pin 262, enabling the first arm 252 and second arm 254 to spread apart as the wedge 264 is pulled toward the proximal end 253 by the cable 268. The cable 268 may be pulled by turning the winding mechanism 266. As the first and second arms 252, 254 separate, they cause distraction of the cephalad and caudal vertebral elements distally while maintaining the proximal position.

Various embodiments of an expanding fusion cage device 300 are shown in FIGS. 21-23 and 28. The fusion cage device 300 may have a generally rectangular or trapezoidal shape in an undeployed position. The fusion cage device 300 may be narrower at a distal end 310 than at the proximal end 308 in the undeployed position. In the deployed position the fusion cage device 300 will have a generally trapezoidal shape. The fusion cage device 300 may include a superior portion 302 adjacent to an inferior portion 304 and separated by an opening 306. The opening 306 may extend from a proximal end 308 to a distal end 310. The proximal end 308 may also include a pathway 312 and a locking mechanism 314. The pathway 312 may extend from the proximal end 308 to the distal end 310. The pathway 312 may taper as it extends from the proximal end 308 to the distal end 310. The tapered pathway 312 may enable an expanding member 316, such as a screw, to expand the distal end 310 of the device 300 as the expanding member 316 is inserted farther into the pathway 312. The pathway 312 may also be threaded 318 to correspond to the threads 320 on the expanding member 316. The expanding member 316 may include a shaft 324 with a head 326 at a first end which may include a drive opening 322 for advancing the expanding member 316 down the pathway 312. Once the shaft 324 of the expanding member 316 is fully inserted into the pathway 312 the locking mechanism 314 may secure the head 326 of the expanding member 316 into the device 300. The locking mechanism 314 may be a locking collar, although other locking mechanisms are also contemplated, such as a cam lock 328, as illustrated in FIG. 28.

The expanding member 316 may be provided in a number of sizes, as illustrated in FIGS. 24-27, depending on the desired expansion of the distal end 310. The expanding member 316 shown in FIG. 24 will provide the largest expansion of the distal end 310 of device 300, while the expanding member 316 illustrated in FIG. 27 will provide the smallest expansion of the distal end 310 of device 300 and the expanding members 316 of FIGS. 25 and 26 will provide intermediate amounts of expansion of the distal end 310. As illustrated, the longer the length of the expanding member 316 the greater the height of expansion the device 300 experiences at its distal end 310.

The obliquely expanding fusion cage devices 10, 50, 80, 100, 150, 200, 250, and 300 may be made of a variety of biocompatible materials, such as, stainless steel, titanium, PEEK, and the like. The devices 10, 50, 80, 100, 150, 200, 250, and 300 may be coated with a substance or material, such as, plasma coating or surface etching, to assist with biocompatibility and help reduce wear. The devices 10, 50, 80, 100, 150, 200, 250, and 300 may also come in various sizes. For example, the devices 10, 50, 80, 100, 150, 200, 250, and 300 may have undeployed heights ranging from approximately six to eighteen millimeters, undeployed widths ranging from approximately eight to fifteen millimeters, and undeployed lengths ranging from approximately twenty to thirty-five millimeters.

The fusion cage devices 10, 50, 80, 100, 150, 200, 250, and 300 may be implanted into a patient using various approaches, however, it is preferred that the devices 10, 50, 80, 100, 150, 200, 250, and 300 are implanted either posterior-laterally or laterally to avoid complications that may be associated with anterior surgery. A unilateral, minimally invasive approach and technique may be used to insert the devices 10, 50, 80, 100, 150, 200, 250, and 300 into a patient. The fusion cage devices 10, 50, 80, 100, 150, 200, 250, and 300 may also be packed with autologous bone to assist in fusion. Some of the devices 10, 50, 80, 100, 150, 200, 250, and 300 may include channels which allow for internal packing of autologous bone pieces. In addition or alternatively, autologous bone pieces may be inserted around the devices 10, 50, 80, 100, 150, 200, 250, and 300 after implantation to assist with fusion of the vertebrae.

The devices 10, 50, 80, 100, 150, 200, 250, and 300, discussed above, may more accurately engage the anatomy of the intervertebral disc space, thus decreasing the incidence of pseudoarthrosis and cage migration. The devices 10, 50, 80, 100, 150, 200, 250, and 300 also allow for oblique expansion which may allow for unilateral application of the devices 10, 50, 80, 100, 150, 200, 250, and 300 to the intervertebral body space using a minimally invasive approach. In addition, the expanding members, discussed above with reference to devices 10, 50, 80, 100, 150, 200, 250, and 300, allow for insertion and removal, if necessary, of the devices 10, 50, 80, 100, 150, 200, 250, and 300.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. An oblique expanding fusion cage device, comprising:
    a body with a superior portion and an inferior portion, wherein the superior portion and the inferior portion each have a proximal end and a distal end;
    an opening from the proximal end of the device to the distal end of the device between the superior portion and inferior portion;
    a hole in the proximal end of the body enabling access to the opening; and
    an expanding member removably inserted into the hole and moveable toward the distal end of the body, wherein the expanding member engages the superior portion and the inferior portion as the expanding member moves distally within the opening,
    wherein an exterior of the body is wider at the distal end than at the proximal end along a dimension of an exterior surface of the superior and inferior portions that extends across the opening in a deployed position.

2. The oblique expanding fusion cage device of claim 1, wherein the body has a generally trapezoidal shape in the deployed position.

3. The oblique expanding fusion cage device of claim 1, wherein the opening is tapered from the proximal end to the distal end.

4. The oblique expanding fusion cage device of claim 1, wherein the expanding member engages an interior surface of the superior portion and an interior surface of the inferior portion as the expansion member moves distally within the opening.

5. The oblique expanding fusion cage device of claim 4, wherein the interior surface of the superior portion is positioned at an angled orientation relative to the interior surface of the inferior portion in an undeployed position.

6. The oblique expanding fusion cage device of claim 4, wherein the interior surface of the superior portion is positioned parallel to the interior surface of the inferior portion in the deployed position.

7. The oblique expanding fusion cage device of claim 4, wherein the interior surfaces of the superior and inferior portions are threaded and the expanding member includes threading that engages with the threaded interior surfaces.

8. The oblique expanding fusion cage device of claim 1, wherein the opening is threaded and the expanding member includes threading that engages with the opening threading.

9. The oblique expanding fusion cage device of claim 1, wherein in the deployed position, the distal end of the superior and inferior portions displaces in a cephalad direction and a caudal direction.

10. An oblique expanding fusion cage device, comprising:
    a body with a proximal end and a distal end;
    an opening extending from the proximal end of the device to the distal end of the device;
    a shim positioned within the opening in the body and moveable through the opening; and
    an expanding member removably inserted into the opening and moveable toward the distal end of the body, wherein the expanding member engages an interior surface of the body as the expanding member moves distally within the opening; and
    wherein in a deployed position, the shim extends out of the opening at the distal end of the body and curves to contact at least one of a cephalad endplate or a caudal endplate.

11. The oblique expanding fusion cage device of claim 10, wherein the shim is coupled to the expanding member.

12. The oblique expanding fusion cage device of claim 10, wherein the expanding member translates the shim out of the opening at the distal end of the body.

13. The oblique expanding fusion cage device of claim 10, wherein in a deployed position, the distal end is wider than the proximal end.

14. The oblique expanding fusion cage device of claim 10, wherein the body has a trapezoidal shape in a deployed position.

15. An oblique expanding fusion cage device, comprising:
    a body with a superior portion and an inferior portion, wherein the superior portion and the inferior portion each have a proximal end and a distal end;

a deployment portion located at the distal end of body and moveable relative to the superior portion;

an opening extending from the proximal end to the distal end of the body;

a deployment mechanism removably inserted into the opening and moveable toward the distal end of the body;

wherein the deployment mechanism engages the deployment portion and moves the deployment portion from a parallel orientation to a perpendicular orientation; and wherein the cage device has a trapezoidal shape in at least one of a deployed position and an undeployed position.

16. The oblique expanding fusion cage device of claim 15, wherein the deployment portion is hingedly coupled to the distal end of the superior portion.

17. The oblique expanding fusion cage device of claim 15, wherein the cage device has a trapezoidal shape in the deployed position.

18. The oblique expanding fusion cage device of claim 15, wherein the deployment mechanism is a screw.

19. The oblique expanding fusion cage device of claim 15, wherein the cage device has a trapezoidal shape in the undeployed position.

20. The oblique expanding fusion cage device of claim 15, wherein the cage device has a trapezoidal shape in the deployed position and undeployed position.

* * * * *